United States Patent [19]

Kalopissis et al.

[11] Patent Number: 4,675,130

[45] Date of Patent: * Jun. 23, 1987

[54] PROCESS FOR PRODUCING INDOANILINES AND KERATIN FIBER DYE COMPOSITION CONTAINING THE SAME

[75] Inventors: Gregoire Kalopissis, Paris; Andree Bugaut, Boulogne-sur-Seine; Francoise Estradier, Paris, all of France

[73] Assignee: L'Oreal, Paris, France

[ * ] Notice: The portion of the term of this patent subsequent to Feb. 15, 1994 has been disclaimed.

[21] Appl. No.: 181,468

[22] Filed: Aug. 26, 1980

Related U.S. Application Data

[60] Division of Ser. No. 910,901, May 30, 1978, Pat. No. 4,246,181, which is a continuation of Ser. No. 598,874, Jul. 24, 1975, abandoned, which is a division of Ser. No. 336,802, Feb. 28, 1973, Pat. No. 3,929,403, which is a continuation-in-part of Ser. No. 97,395, Dec. 11, 1970, abandoned, which is a continuation-in-part of Ser. No. 45,564, Jun. 11, 1970, abandoned.

[30] Foreign Application Priority Data

Jun. 11, 1969 [LU] Luxembourg .......................... 58848

[51] Int. Cl.$^4$ ............................................. C07C 97/18
[52] U.S. Cl. ................................................ 260/396 N
[58] Field of Search ................................... 260/396 N

[56] References Cited

U.S. PATENT DOCUMENTS

| | | | |
|---|---|---|---|
| 1,691,517 | 11/1923 | Goeschke ........................ | 260/396 N |
| 2,472,911 | 6/1949 | Martin ................................ | 260/338 |
| 3,036,875 | 5/1962 | Schlack et al. ..................... | 8/32 |
| 3,078,283 | 2/1963 | Hay .................................... | 260/396 R |
| 3,563,684 | 2/1971 | Charle et al. ........................ | 8/11 |

FOREIGN PATENT DOCUMENTS

| | | | |
|---|---|---|---|
| 370787 | 2/1907 | France . | |
| 44-21197 | 9/1969 | Japan ............................. | 260/396 N |
| 131839 | 7/1971 | Netherlands . | |
| 436574 | 11/1967 | Switzerland . | |

OTHER PUBLICATIONS

Chem. Abstracts, 75:755762.
Chem. Abstracts, 24:3944.
Chem. Abstracts, 41:2901h.
Corbett et al, J. Chem. Soc. (B)(London), May, 1970 pp. 1418–1427.
Suzawa et al, Chemical Abstracts, 57:1109g (1962).

*Primary Examiner*—Werren B. Lone
*Attorney, Agent, or Firm*—Cushman, Darby & Cushman

[57] ABSTRACT

A two-stage process for producing indoanilines includes oxidizing in a first stage a paraphenylene diamine to a quinone diimine and in a second stage condensing the said quinone diimine with a phenolic compound. The resulting indoanilines can be incorporated into a dye composition for keratinous fibers, especially, human hair.

3 Claims, No Drawings

PROCESS FOR PRODUCING INDOANILINES AND KERATIN FIBER DYE COMPOSITION CONTAINING THE SAME

This is a division of application Ser. No. 910,901, filed May 30, 1978, now U.S. Pat. No. 4,246,181, which is a continuation of Ser. No. 598,874, filed July 24, 1975, now abandoned, which is a divisional of Ser. No. 336,802 filed Feb. 28, 1973, now U.S. Pat. No. 3,929,403, which is a continuation-in-part of Ser. No. 97,395 filed Dec. 11, 1970, now abandoned, which is a continuation-in-part of Ser. No. 45,564 filed June 11, 1970, now abandoned.

The present invention relates to a new dye composition for keratinous fibers, especially for human hair and, more particularly, to a dye composition containing in solution at least one indoaniline having the formula:

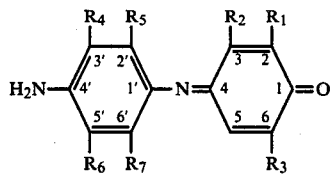

wherein $R_1$ and $R_3$, each independently represent a member selected from the group consisting of hydrogen, halogen, lower alkyl, lower alkoxy, a ureido radical and —NHCOR group wherein R is lower alkyl;

$R_2$ represents a member selected from the group consisting of hydrogen, halogen, lower alkyl, lower alkoxy, a ureido radical, —NHCOR wherein R is lower alkyl and —NHR$_8$ wherein R$_8$ represents a member selected from the group consisting of hydrogen, lower alkyl, hydroxy lower alkyl and carbamylmethyl with the proviso that when $R_2$ is —NHR$_8$, $R_3$ is not hydrogen;

$R_4$, $R_5$, $R_6$ and $R_7$ each independently represent a member selected from the group consisting of hydrogen, halogen, lower alkyl and lower alkoxy radical, it being understood that the terms lower alkyl or alkoxy mean those having 1 to 4 carbon atoms and that the above formula does not exclude the tautomeric forms of these compounds.

The dye compositions of the invention can be aqueous solutions, including aqueous solutions of a lower alkanol. Additionally, the aqueous solutions can include a cosmetic resin, especially when a colored hair set lotion is contemplated.

The dye composition of the present invention contains from about 0.02 to 0.3% by weight, preferably, between about 0.05 to 0.2% by weight of said indoaniline.

The indoaniline as defined above can be used alone, in which case tints varying from purple to blue-green are obtained or in admixture with other capillary dyes such as azo or anthraquinone dyes.

The pH of the dye composition of the present invention can vary within wide limits, and generally the pH will range between 5 and 11, and preferably between 7 and 11.

As stated above the dye composition of this invention can be in the form of an aqueous solution including an aqueous lower alkanol solution, but it can also contain conventionally employed cosmetic thickeners and thus take the form of creams or gels.

The dye composition of the present invention can additionally include various ingredients that are customarily used in cosmetics, such as wetting agents, dispersants, swelling agents, penetrating agents, emollients or perfumes and it can also be packaged in aerosol cans using conventional propellants such as the chlorofluorohydrocarbons.

The dye composition of the present invention is readily prepared by dissolving in water or in a mixture of water and a lower alkanol such as ethanol and isopropanol, one or more indoanilines as defined above, alone, or in admixture with another dye.

The dyeing of keratinic fibers, particularly human hair, by means of the dye composition of the invention can be effected in the usual way be applying the composition on the fibers that are to be dyed, permitting it to remain in contact with the fibers for about 5 to 30 minutes, rinsing the fibers and, if desired, washing the fibers, followed by drying the thus dyed fibers.

When the dye composition of the present invention is to be included in a hair set lotion, conventional cosmetic film-forming resins can usefully be employed therewith. These conventional resins include polyvinylpyrrolidone, copolymers of polyvinylpyrrolidone and vinyl acetate, copolymers of vinyl acetate and an unsaturated carboxylic acid such as crotonic acid, copolymers resulting from the copolymerization of vinyl acetate, crotonic acid and an acrylic or methylacrylic ester, copolymers resulting from the copolymerization of vinyl acetate and a vinyl alkyl ether, copolymers resulting from the copolymerization of vinyl acetate, crotonic acid and a vinyl ester of a long carbon acid or an allyl or methallyl ester of a long carbon chain acid, copolymers resulting from the copolymerization of an ester formed from an unsaturated alcohol and a short carbon chain acid, an unsaturated short carbon chain acid and at least one ester formed from a saturated alcohol and an unsaturated short carbon chain acid, and copolymers resulting from the copolymerization of at least one unsaturated ester and at least one unsaturated acid.

Representative specific cosmetic film-forming resins include polyvinylpyrrolidone having a molecular weight ranging from about 10,000 to 700,000, copolymers of vinylpyrrolidone and vinyl acetate wherein the ratio of PVP to PVA ranges between 30:70–70:30, copolymers of maleic anhydride and butyl vinyl ether, copolymers of vinyl acetate and allyl stearate and allyloxy acetic acid, copolymer of methyl methacrylate and stearyl methacrylate and dimethyl methacrylate, and the like. These resins are utilized in a proportion of about 1 to 3% by weight of the total composition.

The alcohols suitable for preparation of such hair set lotions are lower alkanols, preferably ethanol and isopropanol, which are present in amounts of about 20 to 50% by weight of the total hair set lotion composition. These lotions are utilized in the customary way by applying the same to set hair which has been washed and rinsed, followed by folling up and drying the hair.

Among the indoanilines having the formula set forth above, those in which at least two of the radicals $R_1$ to $R_7$ are not hydrogen atoms and in which $R_5$ and $R_7$ are not both chlorine atoms are new compounds and thus these new compounds are also an embodiment of the present invention.

The indoanilines, useful in the dye compositions of this invention, including the novel indoanilines of this invention can be prepared according to two different processes, one of which is a further embodiment of the present invention, the other having already been known in the art.

Thus, a conventional process for preparing the indoanilines comprises condensing a paraphenylene diamine of the formula:

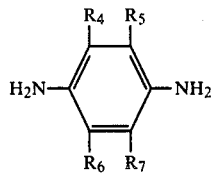

wherein $R_4$, $R_5$, $R_6$ and $R_7$ have the meanings given above with a phenol of the formula:

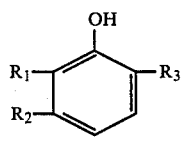

wherein $R_1$, $R_2$ and $R_3$ also have the meanings given above. The condensation reaction is effected in an aqueous medium with a pH ranging from about 8 to 11, in the presence of an oxidizing agent and at a temperature between 0° and 40° C.

The oxidizing agent used in this condensation reaction can be, for example, hydrogen peroxide, potassium persulfate, potassium ferricyanide or sodium hypochlorite and is present, generally in amounts ranging from about 10 to 70 weight percent of the total weight of the paraphenylene diamine and phenol reactants.

Representative phenols that can be used to prepare the compounds of the invention include phenol, 2,6-xylenol, 2,5-xylenol, 5-amino-2-methyl phenol, 5-amino-2-chloro phenol, N-5-methylamino-2-methyl phenol, N-5-carbamylmethylamino-2-methyl phenol, 2,6-dimethyl-3-amino phenol, N-3-acetylaminophenol, N-5-acetylamino-2-methyl phenol, N-2-acetylamino phenol and N-3-acetylamino-2,6-dimethylphenol.

Suitable paraphenylene diamines which can be used in preparation of the indoanilines of the invention are, for example, paraphenylene diamine, paratoluene diamine, 2,5-diamino anisole, 2,5-diamino chlorobenzene, 2-methoxy-5-methyl-paraphenylene diamine, 2,6-dimethyl-3-methoxyparaphenylene diamine and 1,4-diaminodurene.

The mole ratio of paraphenylene diamine to phenol can range between about 3/1 to 1/1 and is preferably 1/1.

The indoanilines of this invention in which at least two of the $R_4$, $R_5$, $R_6$ and $R_7$ radicals are not hydrogen atoms can also be prepared according to a novel process of this invention. This novel process comprises oxidizing a paraphenylene diamine as defined above to a quinone diimine in a first stage, the formula of the said quinone diimine being:

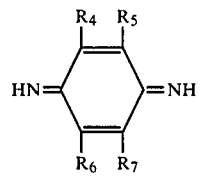

wherein $R_4$, $R_5$, $R_6$ and $R_7$ have the above meanings, and condensing in a second stage the resulting quinone diimine on a phenol compound also as defined above.

Oxidation of the starting paraphenylene diamine to quinone diimine is effected by heating the paraphenylene diamine to a temperature between 30° and 70° C. in an anhydrous solvent such as ethyl ether or isopropyl ether in the presence of a mild oxidizing agent such as silver oxide or lead oxide. The amount of oxidizing agent will range between about 1.5 to 2 moles for 1 mole of the paraphenylene diamine, and is preferably 1,5 mole for 1 mole of this compound.

The resulting quinone diimine is separated from the reaction mass by any convenient separation technique such as by filtration, followed by evaporation of the filtrate to dryness with purification by recrystallization in an anhydrous solvent before being condensed on the phenol compound, the condensation reaction being effected at a temperature ranging from about ambient temperature to about 40° C. either in an aqueous medium, preferably one containing ammonia in amounts of about 2 to 4 weight percent of the total aqueous medium, or in an inert solvent, e.g. ether or benzene. Generally the mole ratio of quinone diimine to phenol is 1/1.

The quinone diimines prepared in the first stage of this new process of the invention are, with the exception of duroquinone diimine, new compounds.

The following examples are intended to illustrate the different aspects of the present invention. The temperature indicated in these examples is in Celsius and, unless otherwise specified, all parts and percentages are by weight.

EXAMPLE 1

N-[(4'-amino-3',5'-dimethyl-2'-methoxy)phenyl]benzoquinone imine is prepared in accordance with the following reaction:

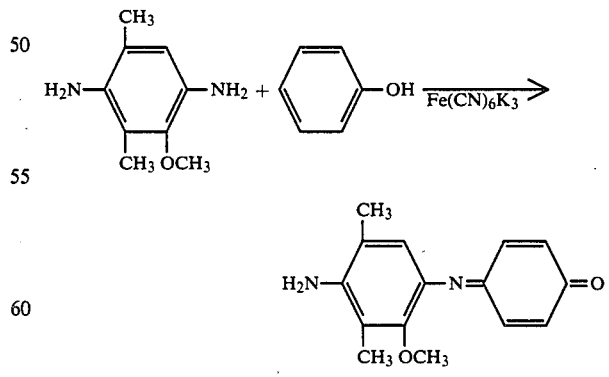

0.023 mole (6 g) 2,6-dimethyl-3-methoxy-paraphenylene diamine dihydrochloride is dissolved in 250 cc water to which 12.5 cc ammonia of 22° Bé strength have been added. The solution thus obtained is added to 0.025 mole (2.35 g) phenol previously dissolved in 250 cc water to which 75 cc ammonia of 22° Bé strength have been added. There is then added to this mixture, with vigorous agitation, 0.05 mole (16.45 g) of potassium ferricyanide in solution in 300 cc water. After having allowed the mixture to stand for one hour at 10° it is then filtered on a suction filter and washed with water, the said resulting product being the above-identified indoaniline in a yield of 2.3 g which, after recrystallization in an acetone-water mixture, melts at 127°.

| Analysis | Calculated for $C_{15}H_{16}N_2O_2$ | Found | |
|---|---|---|---|
| C % | 70.31 | 70.73 | 71 |
| H % | 6.25 | 6.23 | 6.34 |

EXAMPLE 2

N-[(4'-amino-3',5'dimethyl 2'-methoxy)phenyl]2,6-dimethyl benzoquinone imine is prepared in accordance with the following reaction:

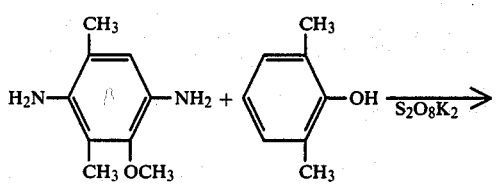

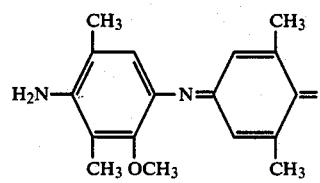

A first solution is prepared by dissolving 0.05 mole (14.34 g) 2,6-dimethyl-3-methoxy paraphenylene diamine dihydrochloride in 500 cc of a 0.2N NaOH solution. A second solution is prepared by dissolving 0.05 mole (7.32 g) 2,6-xylenol in 500 cc of a 0.2N NaOH solution. The two solutions are then mixed and to the resulting mixture there is slowly added, with agitation, 0.05 mole (13.50 g) potassium persulfate dissolved in 500 cc water. When the addition is finished, the reaction mixture is allowed to stand for one hour at 0°. The above-identified indoaniline is then recovered by filtering the reaction mass on a suction filter, the yield amounting to 10.6 g. After recrystallization in an acetone-water mixture, the said indoaniline recovered melts at 123°.

| Analysis | Calculated for $C_{17}H_{20}N_2O_2$ | Found | |
|---|---|---|---|
| C % | 71.83 | 72.04 | |
| H % | 7.04 | 6.99 | |
| N % | 9.85 | 9.91 | 10.10 |

EXAMPLE 3

N-[(4'-amino-3',5'dimethyl-2'methoxy)phenyl]2,5-dimethyl benzoquinone imine is prepared in accordance with the following reaction:

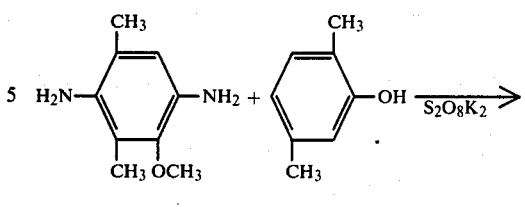

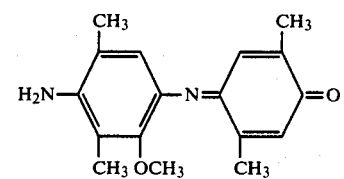

A first solution is prepared by dissolving 0.06 mole (14.34 g) 2,6-dimethyl 3-methoxy-paraphenylenediamine dihydrochloride in 600 cc of a 0.2N NaOH solution. A second solution is prepared by dissolving 0.06 mole (7.32 g) 2,5-xylenol in 600 cc of a 0.2N NaOH solution. These two solutions are mixed and there is then slowly added thereto, with agitation, a solution of 0.06 mole (16.20 g) potassium persulfate in 600 cc water. When the addition is completed, the resulting mixture is allowed to stand for one hour at ambient temperature and then the 9.1 g indoaniline are separated by filtering the reaction mass on a suction filter. After recrystallization in a dimethyl formamide and water mixture, the said indoaniline exhibited a melting point of 124°.

| Analysis | Calculated for $C_{17}H_{20}N_2O_2$ | Found | |
|---|---|---|---|
| C % | 71.83 | 72.03 | |
| H % | 7.04 | 7.04 | |
| N % | 9.85 | 9.55 | 9.75 |

EXAMPLE 4

N-[(4'-amino)phenyl]5-amino-2-methyl benzoquinone imine is prepared in accordance with the following reaction:

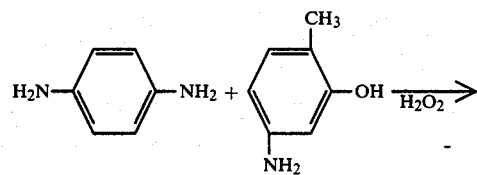

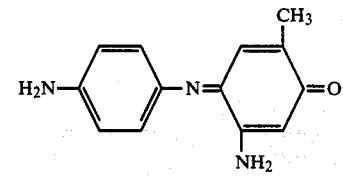

To a solution of 0.03 mole (5.44 g) paraphenylenediamine dihydrochloride dissolved in 100 cc water, ammonia is added in amounts sufficient to adjust the pH thereof to 8. This solution is immediately added to a solution of 0.01 mole (1.23 g) 5-amino 2-methyl phenol in 100 cc water. 30 cc ammonia 22° Bé and 150 cc hydrogen peroxide to make 20 volumes are then added to this mixture which is then allowed to stand for 10 hours at room temperature. 2 g of the said indoaniline in crystalline form is recovered by filtering the reaction mass on a suction filter. After washing with water and acetone and recrystallizing the same from a dimethylformamide and water mixture, the resulting indoaniline had a melting point of 236°.

| Analysis | Calculated for $C_{13}H_{13}N_3O$ | Found | |
|---|---|---|---|
| C % | 68.72 | 68.65 | 68.51 |
| H % | 5.72 | 5.93 | 5.74 |
| N % | 18.50 | 18.29 | 18.25 |

EXAMPLE 5

N-[(4'-amino-3'-methyl)phenyl]3-amino 6-methyl benzoquinone imine is prepared in accordance with the following reaction:

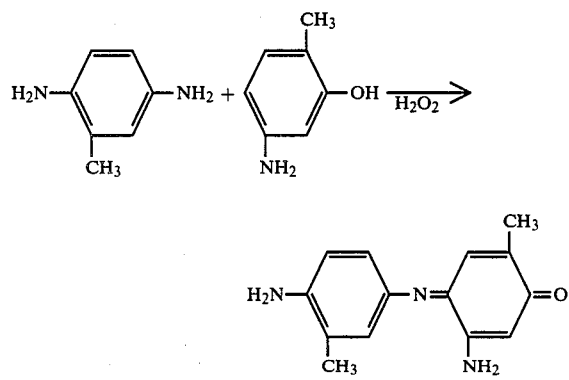

0.025 mole (4.87 g) paratoluylenediamine dihydrochloride is dissolved in 200 cc water and is made alkaline with sufficient ammonia to bring the pH thereof to 8. This solution is immediately added to a solution of 0.02 mole (2.46 g) 5-amino 2-methyl phenol in 200 cc water to which 60 cc ammonia 22° Bé are added. To the resulting mixture thus obtained there is added, little by little, in the course of 20 minutes with agitation, 0.05 mole (16.45 g) potassium ferricyanide dissolved in 250 cc water.

1.5 g of the above indoaniline is recovered by filtering the reaction mass on a suction filter and it are then washed with water. After recrystallization in a pyridine and water mixture, the said indoaniline, melting at 130°, is recovered.

| Analysis | Calculated for $C_{14}H_{15}N_3O$ | Found | |
|---|---|---|---|
| C % | 69.71 | 68.24 | 68.40 |
| H % | 6.22 | 6.17 | 6.18 |
| N % | 17.42 | 17.03 | 17.01 |

EXAMPLE 6

N-[4'-amino-2'-methoxy)phenyl]3-amino 6-methyl benzoquinone imine is prepared in accordance with the following reaction:

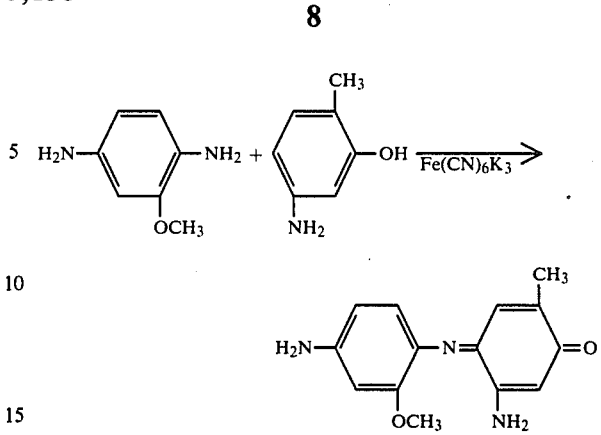

0.0125 mole (2.63 g) 2,5-diamino anisole dihydrochloride is dissolved in 100 cc water, and the resulting solution is made alkaline by addition of 55 cc ammonia 22° Bé. This alkaline solution is then added to 0.0125 mole (1.54 g) 5-amino 2-methyl phenol previously dissolved in 100 cc water, to which there have been added 45 cc ammonia 22° Bé. To the resulting mixture thus obtained there is introduced, little by little, with agitation, 0.025 mole (8.22 g) potassium ferricyanide in solution in 150 cc water. 1.8 g crystalline indoaniline as defined above are recovered by filtering the reaction mass on a suction filter. After washing the same with water and after recrystallizing the said indoaniline from a mixture of dimethylformamide and water, the said indoaniline, melting at 281°, is obtained.

| Analysis | Calculated for $C_{14}H_{15}N_3O_2$ | Found | |
|---|---|---|---|
| C % | 65.37 | 63.99 | 64.35 |
| H % | 5.83 | 5.84 | 6.17 |
| N % | 16.34 | 15.84 | 15.80 |

EXAMPLE 7

N-[(4'-amino 3'-chloro)phenyl]3-amino 6-methyl benzoquinone imine is prepared in accordance with the following reaction:

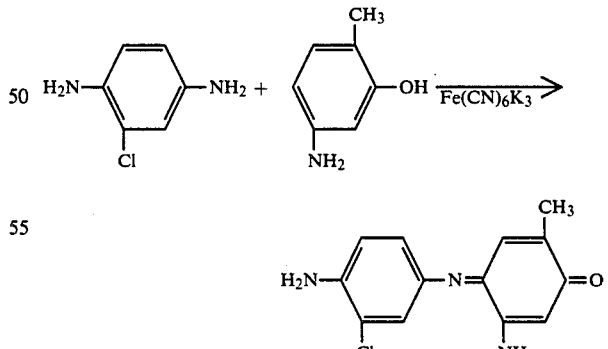

0.02 mole (2.46 g) 5-amino 2-methyl phenol and 0.02 mole (2.85 g) chloroparaphenylene diamine are dissolved in 200 cc water to which have been added 50 cc ammonia 22° Bé. To this mixture there is added, little by little with agitation, 0.04 mole (13.16 g) potassium ferricyanide. The reaction mass is then filtered on a suction filter and a yield of 5 g of said indoaniline is obtained.

After recrystallization in a pyridine and water mixture, the said indoaniline recovered melts at 120°.

| Analysis | Calculated for C$_{13}$H$_{12}$N$_3$ClO | Found | |
|---|---|---|---|
| C % | 59.66 | 58.66 | |
| H % | 4.58 | 4.80 | |
| N % | 16.06 | 15.66 | 15.80 |

EXAMPLE 8

N-[4'-amino 3',5'-dimethyl 2' methoxy)phenyl]3-amino 6-methyl benzoquinone imine is prepared in accordance with the following reaction:

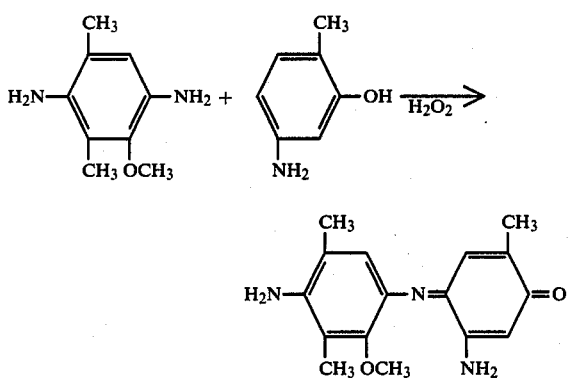

0.0113 mole (2.7 g) 2,6-dimethyl 3-methoxy paraphenylene diamine is dissolved in 75 cc water to which 3 cc ammonia 22° Bé have been added. This solution is then immediately added to 0.0075 mole (0.92 g) 5-amino 2-methyl phenol previously dissolved in 75 cc water. 22 cc ammonia 22° Bé and 100 cc hydrogen peroxide to make 20 volumes are added to this mixture which is then allowed to stand at room temperature for 15 hours. 0.95 g of the above indoaniline is then recovered by filtering the reaction mixture on a suction fil the said recovered indoaniline melting at 205° after recrystallization in a mixture of pyridine and water.

| Analysis | Calculated for C$_{16}$H$_{19}$N$_3$O$_2$ | Found |
|---|---|---|
| C % | 67.36 | 67.47 |
| H % | 6.66 | 6.73 |

EXAMPLE 9

N-[(4'-amino tetramethyl)phenyl]5-amino 2-methyl benzoquinone imine is prepared in accordance with the following reaction:

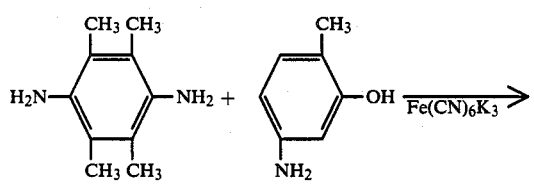

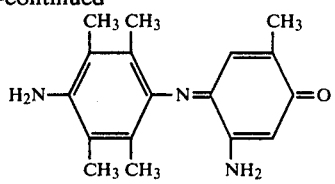

To 200 cc water to which there have been added 10 cc ammonia 22° Bé, there are added, with agitation, 0.02 mole (4.74 g) 1,4 diamino durene dihydrochloride, and a solution of 0.02 mole (2.46 g) 5-amino 2-methyl phenol in 200 cc water containing 75 cc ammonia 22° Bé. Into this mixture there is then introduced, little by little, 0.04 mole (13.16 g) potassium ferricyanide dissolved in 150 cc water. After two hours of agitation, 3.4 g of the above indoaniline are recovered by filtering the reaction mass on a suction filter. A recrystallization in a pyridine and water mixture, the recovered product exhibits a melting point of 222°.

| Analysis | Calculated for C$_{17}$H$_{21}$N$_3$O | Found | |
|---|---|---|---|
| N % | 14.84 | 14.58 | 14.55 |

EXAMPLE 10

N-[(4'-amino 3'-chloro)phenyl]3-amino 6-chloro benzoquinone imine is prepared in accordance with the following reaction:

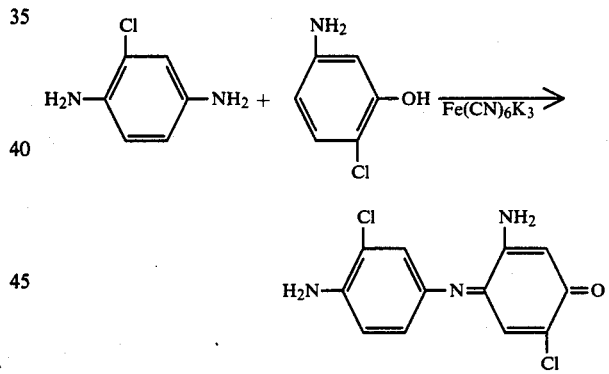

0.02 mole (2.88 g) 5-amino 2-chloro phenol is dissolved together with 0.02 mole (2.85 g) chloroparaphenylene diamine in 500 cc water to which 70 cc ammonia 22° Bé have been added. Into the resulting mixture there is introduced, little by little, with agitation, 0.04 mole (13.20 g) potassium ferricyanide dissolved in 300 cc water. 5.80 g of the above indoaniline in crystalline form which melts at 140° are recovered by filtering on a suction filter the reaction mixture.

| Molecular weight calculated for C$_{12}$H$_9$N$_3$Cl$_2$O | 282 |
|---|---|
| Molecular weight found by potentiometric determination effected with perchloric acid in acetic medium | 281 |

| Analysis | Calculated for C$_{12}$H$_9$N$_3$Cl$_2$O | Found |
|---|---|---|
| C % | 51.06 | 50.95 |
| H % | 3.19 | 3.35 |

| | | | |
|---|---|---|---|
| N % | 14.89 | 14.95 | 14.96 |

EXAMPLE 11

N-[(4'-amino 2'-methoxy)phenyl]6-methyl 3-methylamino benzoquinone imine is prepared in accordance with the following reaction:

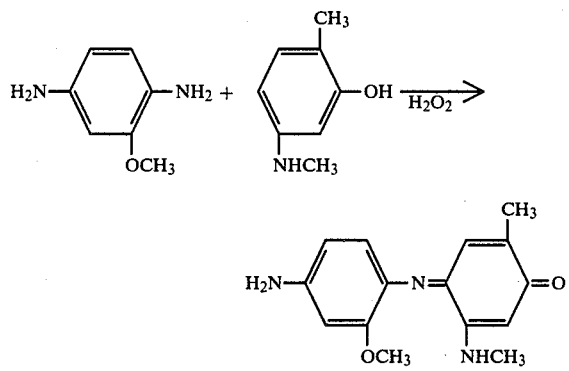

0.05 mole (10.55 g) methoxyparaphenylenediamine dihydrochloride is dissolved in 250 cc water and the pH is adjusted to 8 by addition thereto of ammonia. This solution is immediately added to 0.025 mole (3.5 g) 2-methyl 5-methylamino phenol previously dissolved in 250 cc water and to which 75 cc ammonia 22° Bé have been added. 300 cc hydrogen peroxide are added to the mixture to 20 volumes and then the mixture is allowed to stand at room temperature for 4 hours. By filtering the mixture, there are then obtained 4.17 g of the above indoaniline in crystalline form, which, after washing with water and recrystallization from a mixture of acetone and water, exhibits a melting point of 125°.

| Analysis | Calculated for $C_{15}H_{17}N_3O_2$ | Found | |
|---|---|---|---|
| C % | 66.42 | 66.71 | |
| H % | 6.27 | 6.39 | |
| N % | 15.49 | 15.41 | 15.42 |

EXAMPLE 12

N-[(4'-amino 3'-methyl)phenyl]3-carbamylmethylamino 6-methyl benzoquinone imine is prepared in accordance with the following reaction:

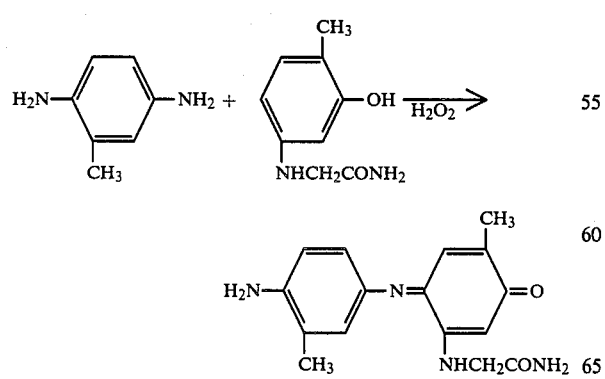

0.1 mole (19.5 g) paratoluylenediamine dihydrochloride is dissolved in 400 cc water. The pH of this solution is adjusted to 8 by addition thereto of ammonia. This solution is immediately added to 0.04 mole (7.2 g) N-5-carbamylmethylamino 2-methyl phenol previously dissolved in 400 cc water. 100 cc ammonia 22° Bé and 500 cc hydrogen peroxide to make 20 volumes are then added to this mixture which is allowed to stand for five hours at ambient temperature. 7.40 g of the above indoaniline in crystalline form are recovered by filtering the reaction mixture on a suction filter. After washing with water and recrystallization from a pyridine and water mixture, the resulting indoaniline exhibited a melting point of 199°.

| Analysis | Calculated for $C_{16}H_{18}O_2N_4$ | Found |
|---|---|---|
| C % | 64.43 | 63.98 |
| H % | 6.04 | 6.08 |

EXAMPLE 13

N-[4'-amino 3'-methyl)phenyl]3-amino-2,6-dimethyl benzoquinone imine is prepared in accordance with the following reaction:

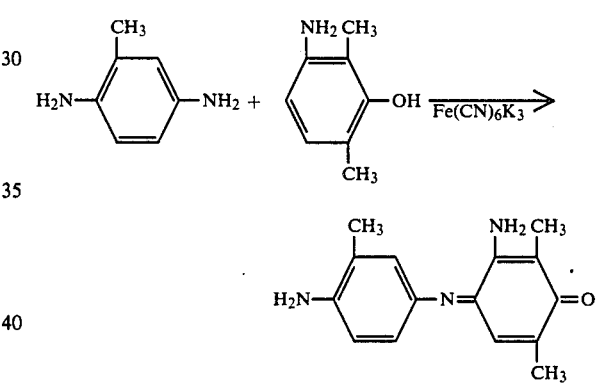

0.025 mole (4.87 g) paratoluylenediamine dihydrochloride is dissolved in 200 cc water and the pH of the solution is adjusted to 8 by addition thereto of ammonia. This solution is immediately added to 0.02 mole (2.74 g) 3-amino-2,6 dimethyl phenol previously dissolved in 200 cc water and to which 60 cc ammonia 22° Bé have been added. To this resulting mixture there is added, little by little, in the course of 20 minutes, with agitation, 0.05 mole (16.45 g) potassium ferricyanide dissolved in 250 cc water.

3.4 g of the above indoaniline are recovered by filtering the reaction mixture on a suction filter. The indoaniline product is then washed with water and after recrystallization from a dimethyl formamide and water mixture, the product exhibits a melting point of 190°.

| Analysis | Calculated for $C_{15}H_{17}N_3O$ | Found | |
|---|---|---|---|
| C % | 70.59 | 70.53 | |
| H % | 6.66 | 6.68 | |
| N % | 16.47 | 16.46 | 16.19 |

EXAMPLE 14

N-[(4'-amino 2'-methoxy)phenyl]3-amino 2,6-dimethyl benzoquinone amine is prepared in accordance with the following reaction:

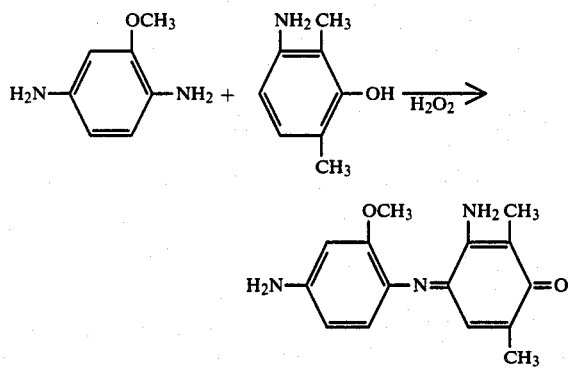

0.01 mole (2.11 g) methoxyparaphenylenediamine dihydrochloride is dissolved in 100 cc water and the pH thereof is adjusted to 8 by addition of ammonia. This solution is immediately added to 0.01 mole (1.37 g) 3-amino 2,6-dimethyl phenol, preliminarily dissolved in 100 cc water. There are added to this resulting mixture 30 cc ammonia 22° Bé and 130 cc hydrogen peroxide to make 20 volumes, and the mixture is allowed to stand at room temperature for four hours. On filtering the reaction mixture on a suction filter there are obtained 1.8 g of the above indoaniline in crystalline form which melts at 217°. After a recrystallization from a mixture of dimethylformamide and water, the said indoaniline exhibited the same melting point.

| Analysis | Calculated for $C_{15}H_{17}N_3O_2$ | Found |
|---|---|---|
| C % | 66.42 | 66.29 |
| H % | 6.27 | 6.36 |
| N % | 15.49 | 15.50 |

EXAMPLE 15

N-[4'-amino 3'chloro)phenyl]3-amino 2,6-dimethyl benzoquinone imine is prepared in accordance with the following reaction:

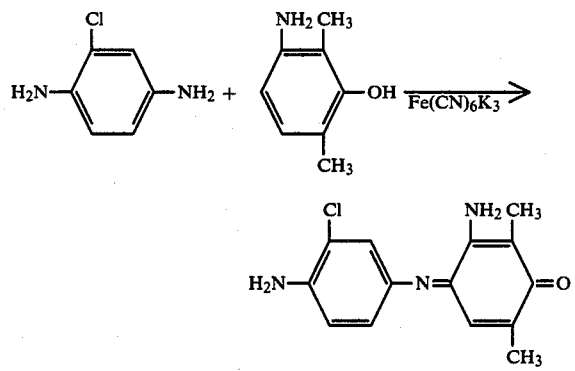

0.02 mole (2.74 g) 3-amino 2,6-dimethyl phenol and 0.02 mole (2.85 g) chloroparaphenylenediamine are dissolved in 200 cc water to which there have been added 50 cc ammonia 22° Bé. Little by little, there is added to this mixture, with agitation, 0.04 mole (13.16 g) potassium ferricyanide. When the addition is completed, 5 g of the above indoaniline are recovered by filtering the reaction mixture on a suction filter The indoaniline is then washed with water and after recrystallization from a mixture of dimethylformamide and water, the product exhibited a melting point of 196°.

| Analysis | Calculated for $C_{14}H_{14}O\ N_3Cl$ | Found | |
|---|---|---|---|
| C % | 60.98 | 60.51 | 60.61 |
| H % | 5.08 | 5.17 | 5.30 |
| N % | 15.24 | 15.17 | 14.95 |
| Cl % | 12.88 | 12.99 | 12.88 |

EXAMPLE 16

N-[(4'-amino 2'-methoxy 5'-methyl)phenyl]3-amino-2,6-dimethyl benzoquinone imine is prepared in accordance with the following reaction:

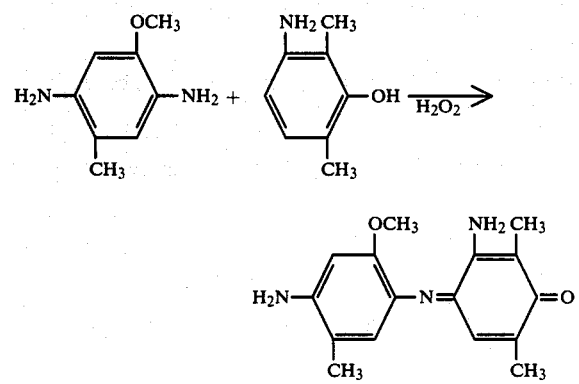

0.2 mole (4.5 g) 2-methoxy-5-methyl paraphenylenediamine dihydrochloride is dissolved in 200 cc water and the pH thereof is adjusted to 8 by the addition thereof of ammonia. This solution is immediately added to 0.02 mole (2.74 g) 3-amino-2,6-dimethyl phenol, previously dissolved in 200 cc water. To the resulting mixture there are added 60 cc ammonia 22° Bé and 260 cc hydrogen peroxide to make 20 volumes. The mixture is allowed to stand at room temperature for four hours. On filtering the reaction mixture on a suction filter, then are obtained 3.1 g of said indoaniline in crystalline form, which after recrystallization from a mixture of pyridine and water, exhibits a melting point of 145°.

| Analysis | Calculated for $C_{16}H_{19}N_3O_2$ | Found | |
|---|---|---|---|
| C % | 67.36 | 66.34 | 66.45 |
| H % | 6.66 | 6.71 | 6.75 |
| N % | 14.73 | 14.80 | 14.63 |

EXAMPLE 17

N-[(4'-amino tetramethyl)phenyl]3-amino-2,6-dimethyl benzoquinone imine is prepared in accordance with the following reaction:

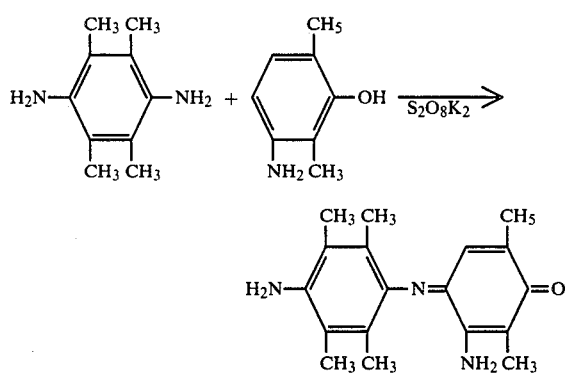

A first solution is prepared by dissolving 0.02 mole (4.74 g) 1,4-diaminodurene dihydrochloride in 200 cc of a 0.2N NaOH solution. A second solution is prepared by dissolving 0.02 mole (2.74 g) 3-diamino-2,6-dimethylphenol in 200 cc of a 0.2N NaOH solution. The two solutions are mixed and there is slowly added thereto, with agitation, 0.02 mole (5.4 g) potassium persulfate in solution in 200 cc water. When the addition is completed, the mixture is allowed to stand for one hour at room temperature. On filtering the reaction mixture on a suction filter 3.7 g of said indoaniline are recovered. After recrystallization from a dimethylformamide and water mixture, the said indoaniline exhibited a melting point of 210°.

| Analysis | Calculated for $C_{18}H_{23}N_3O$ | Found | |
|---|---|---|---|
| N % | 14.14 | 13.87 | 13.89 |

EXAMPLE 18

N-[(4'-amino-3'methyl)phenyl]3-acetylamino benzoquinone imine is prepared in accordance with the following reaction:

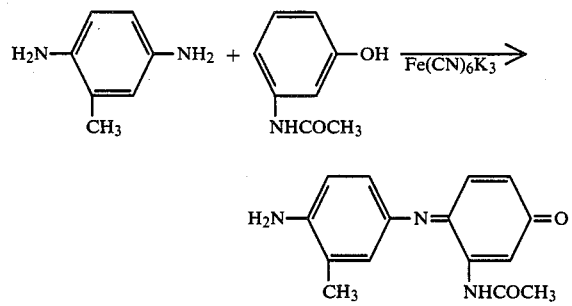

0.4 mole (78 g) paratoluylenediamine dihydrochloride is dissolved in 500 cc water to which 50 cc ammonia 22° Bé have been added. This solution is mixed with 0.4 mole (60.4 g) 3-acetylamino phenol, previously dissolved in two liters of iced water to which one liter ammonia 22° Bé has been added. Into the resulting mixture there is introduced, little by little, in the course of one half hour and with agitation, a solution of 0.8 mole (262 g) potassium ferricyanide in 1300 cc water. On filtering the reaction mixture on a suction filter 50 g of said indoaniline in crystalline form are recovered. This product, after washing with water and then with acetone and recrystallization from a dimethylformamide and water mixture, exhibited a melting point of 141°.

| Analysis | Calculated for $C_{15}H_{15}N_3O_2$ | Found | |
|---|---|---|---|
| C % | 66.91 | 66.50 | 66.52 |
| H % | 5.57 | 5.70 | 5.72 |
| N % | 15.61 | 15.64 | 15.57 |

EXAMPLE 19

N-[(4'-amino-2'-methoxy-5'methyl)phenyl]3-acetylamino benzoquinone imine is prepared in accordance with the following reaction:

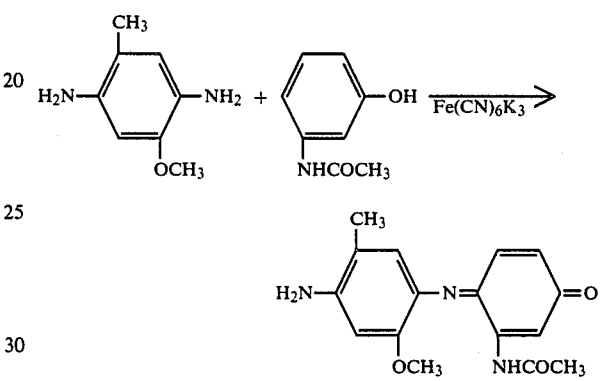

To a solution of 0.02 mole (4.5 g) 2-methoxy-5-methyl paraphenylene diamine dihydrochloride in 200 cc water there are added 10 cm ammonia 22°Be and then 0.02 mole (3.02 g) 3-acetylamino phenol, previously dissolved in 200 cc iced water to which 60 cc ammonia 22°Be have been added. Into the resulting mixture there is introduced, little by little, with agitation, a solution of 0.04 mole (13.1 g) potassium ferricyanide in 250 cc water. After one hour of agitation, the above indoaniline in an ammount of 4.4 g is recovered by filtering the reaction mixture on a suction filter. After recrystallization in a water and pyridine mixture, the said indoanilin exhibited a melting point of 255°.

| Analysis | Calculated for $C_{16}H_{17}O_3N_3$ | Found | |
|---|---|---|---|
| C % | 64.21 | 64.27 | |
| H % | 5.68 | 5.87 | |
| N % | 14.04 | 13.90 | 13.96 |

EXAMPLE 20

N-[(4'-amino)phenyl]5-acetylamino-2-methyl benzoquinone imine is prepared in accordance with the following reaction:

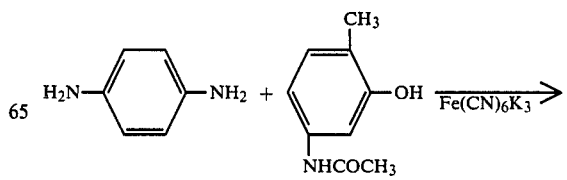

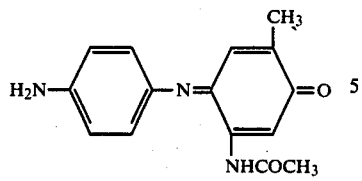

| Analysis | Calculated for $C_{16}H_{17}N_3O_2$ | Found | |
|---|---|---|---|
| C % | 67.84 | 66.37 | 66.50 |
| H % | 6.00 | 6.11 | 6.16 |

0.1 mole (18.1 g) paraphenylenediamine dihydrochloride is dissolved in 100 cc water and the solution is made alkaline by use of 50 cc ammonia 22°Be. This solution is immediately added to 0.1 mole (16.5 g) 5-acetylamino-2-methyl phenol, previously dissolved in one liter of iced water to which 300 cc ammonia 22°Be have been added. Little by little, there is added to this mixture, with agitation, 0.2 mole (65.8 g) potassium ferricyanide dissolved in 1250 cc water. When this addition is completed, 16 g of the above indoaniline are recovered by filtering the reaction mixture on a suction filter. After washing with acetone and recrystallization from a dimethylformamide and water mixture, this indoaniline exhibited a melting point of 105°.

| Analysis | Calculated for $C_{15}H_{15}N_3O_2$ | Found | |
|---|---|---|---|
| C % | 66.91 | 66.11 | |
| H % | 5.57 | 5.75 | |
| N % | 15.61 | 15.52 | 15.47 |

EXAMPLE 21

N-[4'-amino-3'-methyl)phenyl]3-acetylamino-6-methyl benzoquinone imine is prepared in accordance with the following reaction:

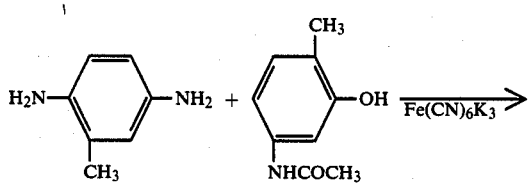

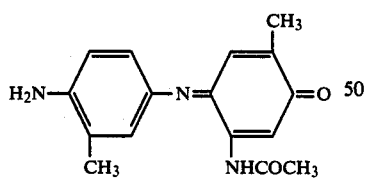

To a solution of 0.02 mole (3.90 g) paratoluylenediamine dihydrochloride in 200 cc water, there are added 100 cc ammonia 22°Be and then 0.02 mole (3.30 g) 5-acetylamino-2-methyl phenol, previously dissolved in 200 cc water to which 60 cc ammonia 22°Be have been added. Into the resulting mixture there is introduced, little by little, with agitation, a solution of 0.04 mole (13.1 g) potassium ferricyanide in 200 cc water. After an hour of agitation, the reaction mixture are filtered off and there is recovered 3.80 g of said indoaniline in crystalline form. After recrystallization from a dimethylformamide and water mixture, the said indoaniline exhibited a melting point of 140°.

EXAMPLE 22

N-[(4'-amino-2'-methoxy)phenyl]3-acetylamino-6-methyl benzoquinone imine is prepared in accordance with the following reaction:

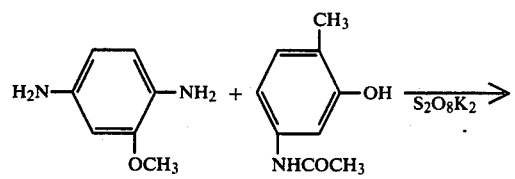

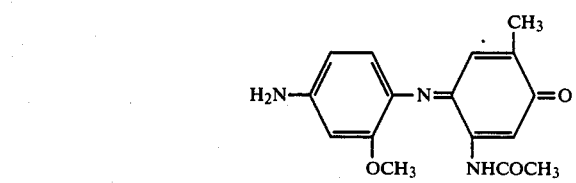

A first solution is prepared by dissolving 0.02 mole (4.22 g) 2,5-diamino anisole dihydrochloride in 200 cc of a 0.2N NaOH solution. A second solution is prepared by dissolving 0.02 mole (3.3 g) 5-acetylamino-2-methyl phenol in 200 cc of a 0.2N NaOH solution. The two solutions are mixed and there is then slowly added, with agitation, 0.02 mole (5.4 g) potassium persulfate, previously dissolved in 250 cc water. When the addition is completed, the reaction mixture is filtered off and 3.1 g of said indoaniline are recovered, which, after recrystallization from a mixture of dimethylformamide and water, exhibited a melting point of 215°.

| Analysis | Calculated for $C_{16}H_{17}O_3N_3$ | Found | |
|---|---|---|---|
| C % | 64.21 | 64.45 | 64.16 |
| H % | 5.68 | 5.90 | 5.82 |
| N % | 14.04 | 14.30 | 14.12 |

EXAMPLE 23

N-[(4'-amino-3'-chloro)phenyl]3-acetylamino-6-methyl benzoquinone imine is prepared in accordance with the following reaction:

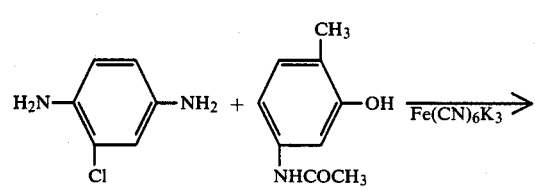

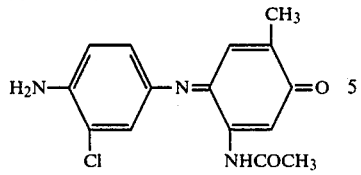

0.02 mole (3.30 g) 5-acetylamino-2-methyl phenol and 0.02 mole (2.85 g) chloroparaphenylene diamine are dissolved in 500 cc water to which there have been added 70 cc ammonia 22°Be. Into the resulting mixture, there is introduced, little by little, with agitation, 0.04 mole (13.16 g) potassium ferricyanide in solution in 300 cc water. On filtering the reaction mixture on a suction filter, 3.8 g of said indoaniline in crystalline form are recovered which, after recrystallization from a mixture of pyridine and water, exhibited a melting point of 215°.

| Molecular weight calculated for $C_{15}H_{14}N_3O_2Cl$ | | 303.5 | |
|---|---|---|---|
| Molecular weight found by potentiometric determination using perchloric acid in an acetic medium | | 292 | |
| Analysis | Calculated for $C_{15}H_{14}N_3O_2Cl$ | Found | |
| C % | 59.31 | 58.48 | |
| H % | 4.64 | 4.67 | |
| N % | 13.83 | 13.69 | 13.79 |

EXAMPLE 24

N-[4'-amino-2'-methoxy-5'-methyl)phenyl]3-acetylamino-6-methyl benzoquinone imine is prepared in accordance with the following reaction:

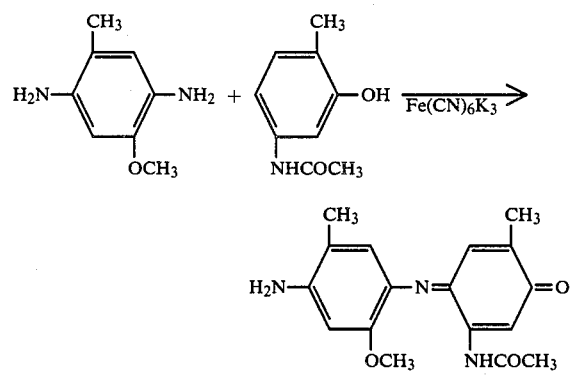

To a solution of 0.02 mole (4.5 g) 2-methoxy-5-methyl paraphenylene diamine dihydrochloride in 200 cc water, there are added 10 cc ammonia 22°Be and then 0.02 mole (3.30 g) 5-acetylamino-2-methyl phenol, previously dissolved in 200 cc iced water to which 60 cc ammonia 22°Be have been added. Into the resulting mixture there is introduced, little by little, with agitation, a solution of 0.04 mole (13.1 g) potassium ferricyanide in 250 cc water. After one hour of agitation, the reaction mixture is filtered off and 5.4 g of said indoaniline are recovered which, after recrystallization from ethyl acetate, exhibited a melting point of 220°.

| Molecular weight calculated for $C_{17}H_{19}N_3O_2$ | 313 |
|---|---|
| Molecular weight found by potentiometric determination effected with perchloric acid in acetic medium | 316 |

| Analysis | Calculated for $C_{17}H_{19}N_3O_2$ | Found | |
|---|---|---|---|
| N % | 13.40 | 13.33 | 13.42 |

EXAMPLE 25

N-[(4'-amino tetramethyl)phenyl]3-acetylamino-6-methyl benzoquinone imine is prepared in accordance with the following reaction:

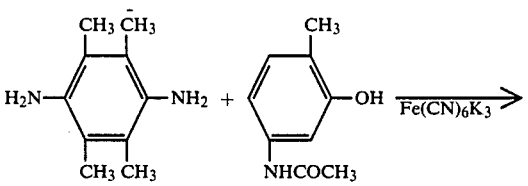

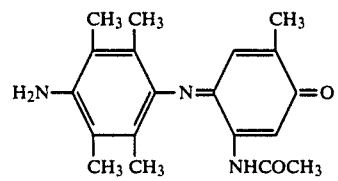

To a solution of 0.02 mole (4.74 g) 1,4-diaminodurene dihydrochloride in 200 cc water, there are added 10 cc ammonia 22°Be and then 0.02 mole (3.30 g) 5-acetylamino-2-methyl phenol, previously dissolved in 200 cc water to which 60 cc ammonia 22°Be had been added. Into the resulting mixture there is introduced, little by little, with agitation, a solution of 0.04 mole (13.1 g) potassium ferricyanide in 200 cc water. After an hour of agitation, the reaction mixture is filtered off and 3.5 g of said indoaniline in crystalline form are recovered, which after recrystallization from a mixture of pyridine and water exhibited a melting point of 270°.

| Molecular weight calculated for $C_{19}H_{23}N_3O_2$ | | 325 | |
|---|---|---|---|
| Molecular weight found by potentiometric determination effected in methylisobutylketone, using perchloric acid | | 337 | |
| Analysis | Calculated for $C_{19}H_{23}N_3O_2$ | Found | |
| C % | 70.15 | 69.87 | 69.81 |
| H % | 7.07 | 7.19 | 7.04 |
| N % | 12.92 | 13.06 | 12.87 |

EXAMPLE 26

N-[(4'-amino-3'methyl)phenyl]2-acetylamino benzoquinone imine is prepared in accordance with the following reaction:

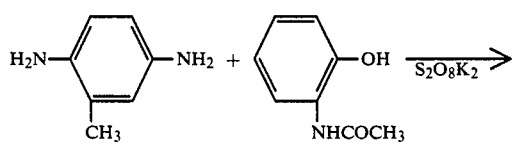

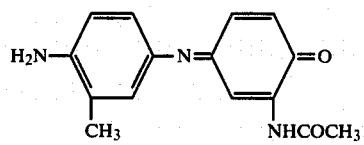

A first solution is prepared by dissolving 0.02 mole (3.90 g) paratoluylenediamine dihydrochloride in 200 cc of a 0.2N NaOH solution. A second solution is prepared by dissolving 0.02 mole (3.02 g) 2-acetylamino phenol in 200 cc of a 0.2N NaOH solution. The two solutions are mixed and there is then slowly added, with agitation, 0.02 mole (5.4 g) potassium persulfate dissolved in 250 cc water. When the addition is completed, the reaction mixture is allowed to stand for one hour at ambient temperature. On filtering the reaction mixture on a suction filter, 4.5 g of said indoaniline are recovered, which after recrystallization from a mixture of dimethylformamide and water, exhibited a melting point of 110°.

| Analysis | Calculated for $C_{15}H_{15}N_3O_2$ | Found | |
|---|---|---|---|
| N % | 15.61 | 15.77 | 15.83 |

EXAMPLE 27

N-[(4'-amino)phenyl]3-acetylamino-2,6-dimethyl benzoquinone imine is prepared in accordance with the following reaction:

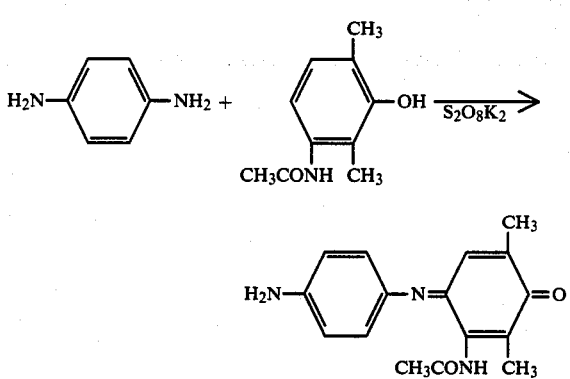

A first solution is prepared by dissolving 0.06 mole (10.9 g) paraphenylene diamine dihydrochloride in 600 cc of a 0.2N NaOH solution. A second solution is prepared by dissolving 0.06 mole (10.8 g) 3-acetylamino-2,6-dimethyl phenol in 600 cc of a 0.2N NaOH solution. The two solutions are mixed and there is then slowly added, with agitation, 0.06 mole (16.2 g) potassium persulfate in solution in 600 cc water. When the addition is completed, the reaction mixture is allowed to stand at room temperature for one hour. The reaction mixture is then filtered off and the above indoaniline is recovered, which after recrystallization from a mixture of dimethylformamide and water exhibited a melting point of 220°.

| Analysis | Calculated for $C_{16}H_{17}O_2N_3$ | Found | |
|---|---|---|---|
| C % | 67.84 | 67.64 | |
| H % | 6.01 | 6.24 | |
| N % | 14.84 | 14.98 | 15.00 |

EXAMPLE 28

The indoaniline of Example 16, i.e. N-[(4'-amino 2'-methoxy 5'-methyl)phenyl]3-amino-2,6-dimethyl benzoquinone imine is prepared in accordance with the following two stage reaction:

1st Stage:

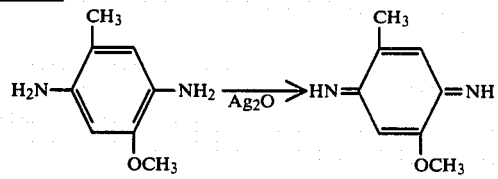

2nd Stage:

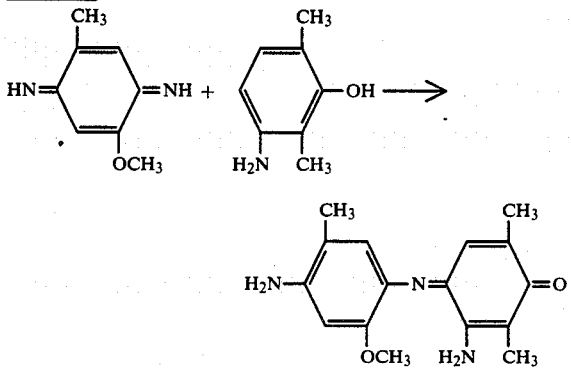

1st Stage:

2-methyl-5-methoxy benzoquinone diimine is prepared as follows:

0.056 mole (8.56 g) 2-methyl 5-methoxy paraphenylenediamine is introduced into 850 cc isopropyl anhydrous ether to which there have been added 0.085 mole (19.7 g) silver oxide and 55 g anhydrous sodium sulfate. The mixture is agitated for two hours, maintaining the temperature thereof between 30° and 40°. After cooling, the sodium sulfate and the silver are separated from the reaction mixture by filtration, and the resulting filtrate is evaporated to dryness under vacuum. The dry residue, after recrystallization from a mixture of benzene-hexane, furnishes 5.8 g 2-methoxy-5-methyl benzoquinone diimine, which has a melting point of 96°.

| Analysis | Calculated for $C_8H_{10}N_2O$ | Found |
|---|---|---|
| C % | 64.00 | 64.17 |
| H % | 6.66 | 6.74 |
| N % | 18.66 | 18.58 |

2nd Stage:

The desired indoaniline, N-[(4'-amino-2'-methoxy-5'-methyl)phenyl]3-amino 2,6-dimethyl benzoquinone imine is prepared as follows:

0.01 mole (1.50 g) 2-methyl 5-methoxy benzoquinone diimine prepared in the first stage of this reaction is dissolved in 100 cc anhydrous ether. 0.01 mole (1.37 g)

3-amino-2,6-dimethyl phenol in solution in 50 cc anhydrous ether is then added to the same. The resulting reaction mixture is allowed to stand for four hours at room temperature, and the solvent is driven off under vacuum, the residue being crystallized in a mixture of pyridine and water. The above indoaniline thus obtained exhibits a melting point of 145°.

| | |
|---|---|
| Molecular weight calculated for $C_{16}H_{19}N_3O_2$ | 285 |
| Molecular weight found by potentiometric determination using perchloric acid in methylisobutylacetone | 277 |

EXAMPLE 29

The indoaniline of Example 19, i.e. N-[(4'amino-2'-methoxy-5'-methyl)phenyl]3-acetylamino benzoquinone imine is prepared in accordance with the following two stage reaction:

1st Stage:

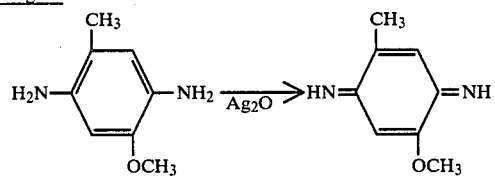

2nd Stage:

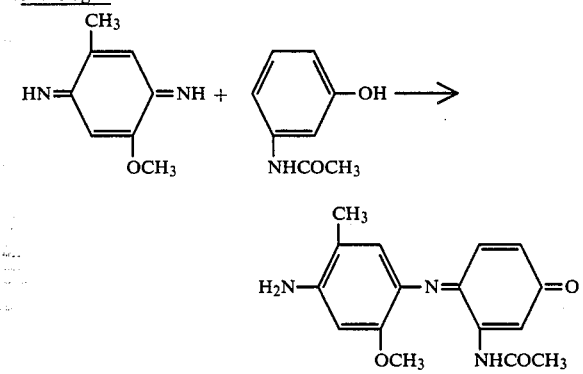

1st Stage:
2-methyl-5-methoxy-benzoquinone imine is prepared essentially in the same manner outlined in the first stage of Example 28.
2nd Stage:
The desired indoaniline, N-[(4'-amino-2'-methoxy-5'-methyl)phenyl]3-acetylamino benzoquinone imine is prepared as follows:

0.003 mole (0.4 g) 3-acetylamino phenol is dissolved in 70 cc water to which 10 cc ammonia 22°Be have been added. To this solution there is added 0.0035 mole (0.52 g) 2-methyl-5-methoxy-benzoquinonediimine from the first stage in solution in 50 cc water. The mixture is agitated for half an hour. The reaction mixture is filtered off and 0.62 g of the above indoaniline is recovered which exhibits a melting point of 252°.

| | |
|---|---|
| Molecular weight calculated for $C_{16}H_{17}O_3N_3$ | 299 |
| Molecular weight found by potentiometric determination using perchloric acid in acetic medium | 290 |

EXAMPLE 30

The indoaniline of Example 8, i.e., N[(4'-amino 3',5'-dimethyl-2'methoxy)phenyl]3-amino 6-methyl benzoquinone imine is prepared in accordance with the following two stage reaction:

1st Stage:

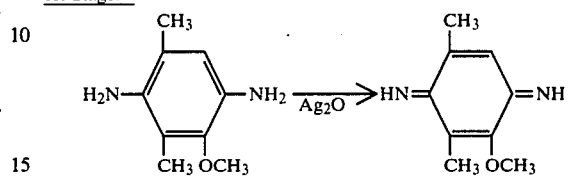

2nd Stage:

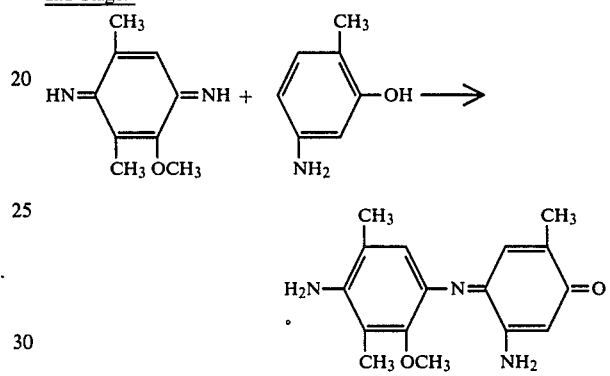

1st Stage:
3,5-dimethyl-2-methoxy benzoquinone diimine is prepared as follows:

0.037 mole (6.10 g) 2-methoxy-3,5-dimethyl paraphenylene diamine is introduced into 350 cc anhydrous ether to which there have been added 0.055 mole (12.7 g) silver oxide and 35 g anhydrous sodium sulfate. The mixture is heated to reflux for two hours with maintenance of good agitation. After cooling, the sodium sulfate and the silver are filtered out and the filtrate is evaporated to dryness under vacuum. The dry residue, which is the above diimine, after recrystallization in cyclohexane exhibits a melting point of 47°.

| Analysis | Calculated for $C_9H_{12}N_2O$ | Found | |
|---|---|---|---|
| N % | 17.07 | 17.25 | 16.82 |

2nd Stage:
The desired indoaniline N-[(4'-amino-3',5'-dimethyl-2'-methoxy)phenyl]3-amino-6-methyl benzoquinone imine is prepared as follows:

0.0028 mole (0.34 g) 5-amino-2-methyl phenol is dissolved in 70 cc water to which 10 cc ammonia 22°Be have been added. To this solution there is added 0.036 mole (0.59 mole) 3,5-dimethyl-2-methoxy benzoquinone diimine from the first stage in 60 cc water. The mixture is agitated for 30 minutes. The reaction mixture is then filtered off and 0.55 g of the above indoaniline is recovered, which exhibits a melting point of 205°.

| | |
|---|---|
| Molecular weight calculated for $C_{16}H_{19}N_3O_2$ | 285 |
| Molecular weight found by potentiometric determination using perchloric acid in | 286 |

| -continued |
|---|
| methylisobutylacetone |

EXAMPLE 31

N-[(4'amino 2',5'dimethoxy)phenyl]3-amino-6-methyl benzoquinone imine is prepared in accordance with the following two stage reaction:

1st Stage:

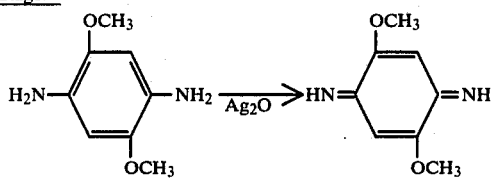

2nd Stage:

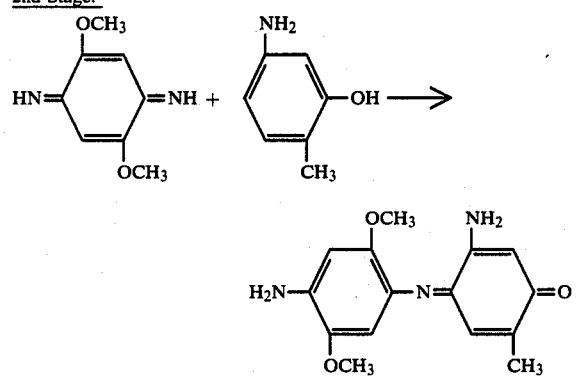

1st Stage:

2,5-dimethoxy benzoquinone diimine is prepared as follows:

0.06 mole (10 g) 2,5-dimethoxy paraphenylene diamine is introduced into a liter of anhydrous isopropyl ether. 21 g silver oxide and 48 g anhydrous sodium sulfate are then added to the same. The resulting mixture is heated at reflux for 6 hours, while maintaining good agitation. After cooling the reaction mixture the sodium sulfate and the silver are filtered out and the filtrate is evaporated to dryness under vacuum. The dry residue which is the above diimine, after recrystallization from a benzene-petroleum ether mixture, yields pure 2,5-dimethoxy benzoquinone diimine having a melting point of 184°.

| Analysis | Calculated for $C_8H_{10}N_2O_2$ | Found | |
|---|---|---|---|
| C % | 57.80 | 57.79 | 57.60 |
| H % | 6.03 | 6.12 | 6.06 |
| N % | 16.87 | 16.80 | 16.85 |

2nd Stage:

The desired indoaniline, i.e. N-[(4'-amino-2',5'-dimethoxy)phenyl]3-amino-6-methyl benzoquinone imine is prepared as follows:

0.02 mole (0.246 g) 3-amino-6-methyl phenol is dissolved in 30 cc water to which 5 cc ammonia 22° Bé were added. To this solution there is added 0.02 mole (0.332 g) 2,5-dimethoxy benzoquinone diimine from the first stage in solution in 60 cc water. The mixture is agitated for 20 minutes. Thereafter the reaction mixture is filtered off, yielding 0.125 g of said indoaniline which exhibits a melting point of 104°.

EXAMPLE 32

The following dye composition, in accordance with the present invention is prepared as follows:

| The indoaniline of Example 2 | 0.15 |
|---|---|
| Water in sufficient quantity to make up | 100 g |
| Ammonia 22° Be' in sufficient quantity for | pH 10 |

The dye composition is applied to 100% white hair for 20 minutes and yields after rinsing and shampooing a blue lavender tint.

EXAMPLE 33

The following dye composition, also in accordance with this invention, is prepared as follows:

| The indoaniline of Example 5 | 0.2 g |
|---|---|
| Butyl glycol | 5 g |
| Lauric alcohol oxyethylenated with 10.5 moles ethylene oxide | 5 g |
| Water in sufficient quantity to make | 100 g |

This dye composition, which has a pH of 7, is applied to 90% grey hair. After a waiting time of 20 minutes, followed by a rinse and shampoo, a purplish violet coloration is obtained.

EXAMPLE 34

Another dye composition of the present invention is prepared as follows:

| The indoaniline of Example 7 | 0.1 g |
|---|---|
| Ammonium lauryl sulfate with 20% lauric alcohol | 20 g |
| Ethylenediamine tetraacetic acid | 0.2 g |
| Ammonia 22° Be' | 1 cc |
| Water in sufficient quantity to make | 100 g |

This dye composition, which has a pH of 11, is applied for 20 minutes to platinum hair. After rinsing and shampooing a rosewood coloration is imparted to the hair.

EXAMPLE 35

Yet another dye composition of the present invention is formulated as follows:

| The indoaniline of Example 11 | 0.05 g |
|---|---|
| Ammonium lauryl sulfate with 20% lauric alcohol | 20 g |
| Ethylenediamine tetraacetic acid | 0.2 g |
| Ammonia 22° Be' | 1 cc |
| Water in sufficient quantity to make up | 100 g |

This dye composition, which has a pH of 11, is applied for 30 minutes to 100% white hair. After rinsing and shampooing, a mauve coloration is obtained.

EXAMPLE 36

The following dye composition is prepared:

| The indoaniline of Example 13 | 0.1 g |
|---|---|
| Butylglycol | 5 g |
| Lauric alcohol oxyethylenated with 10.5 moles ethylene oxide | 5 g |

| | |
|---|---|
| Water in sufficient quantity to make up | 100 g |

This solution, which has a pH of 7, is applied to 100% white hair for 20 minutes. After rinsing and shampooing, a pink coloration is imparted to the hair.

EXAMPLE 37

Still another dye composition in accordance with the present invention is prepared as follows:

| | |
|---|---|
| The indoaniline of Example 20 | 0.1 g |
| Butylglycol | 5 g |
| Lauric alcohol oxyethylenated with 10.5 moles ethylene oxide | 5 g |
| Water in sufficient quantity to make up | 100 g |

This dye composition, which has a pH of 7, is applied for 20 minutes to 100% white hair. After rinsing and shampooing, a mauve tint is imparted to the hair.

EXAMPLE 38

The following dye composition comprises:

| | |
|---|---|
| The indoaniline of Example 26 | 0.1 g |
| Water in sufficient quantity to make up | 100 g |
| Ammonia 22° Be' in sufficient quantity for | pH 9 |

This dye composition is applied to 90% grey hair for 20 minutes and after rinsing and shampooing a blue-grey coloration is imparted to the hair.

EXAMPLE 39

A hair set lotion is formulated in accordance with the present invention:

| | |
|---|---|
| The indoaniline of Example 5 | 0.1 g |
| Copolymer of crotonic acid and vinyl acetate | 2 g |
| 96° titer ethanol in sufficient quantity to make | 50 g |
| Water in sufficient quantity to make up | 100 g |

This hair set lotion is applied to 100% white hair and imparts a purple sheen.

EXAMPLE 40

The following dye composition comprises:

| | |
|---|---|
| The indoaniline of Example 31 | 0.2 g |
| 96° titer ethanol | 20 g |
| Water in sufficient amount to make up | 100 g |
| Ammonia 22° Be' in sufficient quantity for | pH 9.5 |

This dye composition is applied for 20 minutes to 95% white hair. After rinsing and shampooing an ashen-grey coloration is imparted to the hair.

Equally favorable dye compositions and hair set lotions are prepared employing the other indoanilines disclosed hereinbefore.

EXAMPLE 41

Preparation of N-[(amino-4'methoxy-2')phenyl]-dimethyl-2,6benzoquinone imine, having the formula

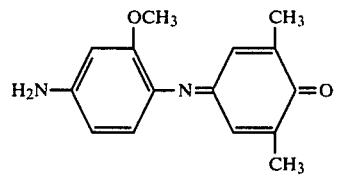

Initially 0.15 mole (31.65 g) of the dihydrochloride of metoxyparaphenylene diamine is dissolved in 900 cc of a 0.33N NaOH solution. Separately, 0.15 mole (18.3 g) of 2,6-xylenol is dissolved in 450 cc of a 0.66N NaOH solution. The two solutions are then mixed, to which mixture there are slowly added with agitation, 34.2 g of ammonium persulfate in 200 cc of water. Thereafter, the reaction mixture is allowed to stand for 10 minutes at ambient temperature. Then, by filtering, there are separated 17.5 g of the above indoaniline, which, after washing with water and with acetone and then drying under vacuum, has a melting point of 182° C. and is chromatographically pure.

Molecular weight calculated for $C_{15}H_{16}N_2O_2 = 256$.

Molecular weight found by potentiometric determination effected in methylisobutylketone using perchloric acid = 261.

| Analysis | Calculated for $C_{15}H_{16}N_2O_2$ | Found | |
|---|---|---|---|
| C % | 70.31 | 70.41 | 70.59 |
| H % | 6.25 | 6.35 | 6.24 |
| N % | 10.94 | 10.65 | 10.76 |

EXAMPLE 42

Preparation of N-[(4'-amino 2',5'-dimethoxy)-phenyl]2,6-dimethyl benzoquinone imine having the formula

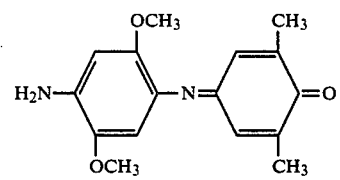

To a solution cooled to 0° C. and containing 2.28 g of ammonium persulfate in 20 cc water, 50 cc of acetone and 10 cc ammonia (22° Bé), there is added 0.01 mole (2.41 g) of the dihydrochloride of 2,5 dimethoxy paraphenylene diamine dissolved in 25 cc of water. This mixture is then immediately added to a solution, which has been cooled in ice, containing 0.01 mole of 2,6-xylenol (1.22 g) in 50 cc of water, 20 cc of ammonia (22° Bé) and 5 cc of acetone. The resulting reaction mixture immediately turns blue-green. There are then added 175 cc of water and, by filtering there are separated 1.2 g of the above indcaniline, which after washing with water and drying under a vacuum, is chromatographically pure and melts at 170° C.

Molecular weight calculated for $C_{16}H_{18}N_2O_3 = 286$.

Molecular weight found by potentiometric determination effected with methylisobutylketone in perchloric acid = 294.

| Analysis | Calculated for $C_{16}H_{18}N_2O_3$ | Found | |
|---|---|---|---|
| C % | 67.13 | 67.00 | 66.81 |
| H % | 6.29 | 6.11 | 6.14 |
| N % | 9.78 | 9.80 | 9.86 |

EXAMPLE 43

Preparation of N-[(4'-amino-2'-methoxy 5'-methyl)-phenyl]6-methyl 3-amino benzoquinone imine, having the formula

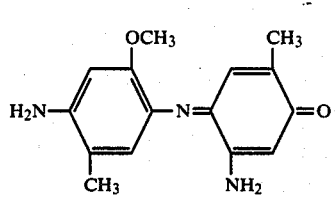

There is dissolved 0.1 mole (12.3 g) of 2-methyl 5-amino phenol in 350 cc of water to which have been added 100 cc of ammonia (22° Bé). To this solution there are added simultaneously through two dropping funnels, a solution of 0.1 mole (22.5 g) of the dihydrochloride of 2-methoxy 5-methyl paraphenylenediamine in 100 cc of water through one of the funnels, and a solution of 0.1 mole (22.8 g) of ammonium persulfate in 50 cc of water through the other, while the reaction mixture is cooled in ice. Thereafter, the reaction mixture is allowed to stand 15 minutes at ambient temperature and there are recovered by filtering 8.8 g of the above indoaniline. After recrystallization in a mixture of pyridine and water and after drying under vacuum, the resulting product exhibited a melting point of 158° C.

| Analysis | Calculated for $C_{15}H_{17}N_3O_2, 0,5\ H_2O$ | Found | |
|---|---|---|---|
| C % | 64.29 | 64.64 | 64.57 |
| H % | 6.42 | 6.66 | 6.57 |
| N % | 15.00 | 15.00 | 14.94 |

EXAMPLE 44

Preparation of N-[(4'-amino)phenyl]3-amino 2,6-dimethyl benzoquinone imine having the formula

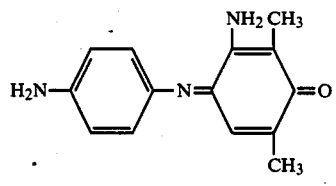

There is dissolved 0.1 mole (13.7 g) of 2,6-dimethyl 3-amino phenol in one liter of water to which have been added 400 cc of ammonia. To the resulting solution there is added 0.1 mole (10.8 g) of paraphenylene diamine in one liter of water. To this resulting mixture there are then added 1300 cc of $H_2O_2$ (20 volumes). The reaction mixture is then allowed to stand for 5 hours at ambient temperature after which 10.5 g of the above indoaniline in crystalline form are separated by filtering. After washing with water, and recrystallization from a mixture of pyridine and water, followed by drying under vacuum, the resulting product exhibited a melting point of 188° C.

| Analysis | Calculated for $C_{14}H_{15}N_3O$ | Found | |
|---|---|---|---|
| C % | 69.70 | 69.30 | 69.21 |
| H % | 6.22 | 6.18 | 6.24 |
| N % | 17.42 | 17.45 | 17.49 |

EXAMPLE 45

Preparation of N-[(4'-amino 2',5'-dimethoxy)-phenyl]2-methyl 5-acetylamino benzoquinone imine having the formula

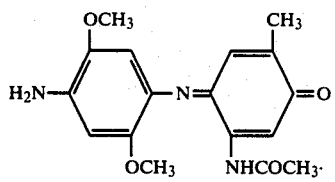

To a solution cooled to 0° C. and containing 2.28 g of ammonium persulfate in 20 cc of water, 50 cc of acetone an 10 cc of ammonia (22° Bé) there is added 0.01 mole (2.41 g) of the dihydrochloride of 2,5-dimethoxy paraphenylene diamine dissolved in 25 cc of water. There is then immediately added to the mixture thus obtained, a solution, cooled in ice, of 0.01 mole (1.65 g) of 2-methyl, 5-acetylamino phenol in 20 cc of 0.5N NaOH solution. The above indoaniline precipitates immediately. The precipitate is filtered and then washed with water and with acetone. The washed precipitate is then dried under vacuum. The resulting indoaniline thus prepared is chromatographically pure and exhibits a melting point of 235° C.

| Analysis | Calculated for $C_{17}H_{19}N_3O_4$ | Found | |
|---|---|---|---|
| C % | 62.01 | 62.30 | 62.02 |
| H % | 5.78 | 5.91 | 5.82 |
| N % | 12.76 | 12.49 | 12.57 |

EXAMPLE 46

Preparation of N-[(4'-amino, 3'-methyl)phenyl]3-acetylamino, 2,6-dimethyl benzoquinone imine having the formula

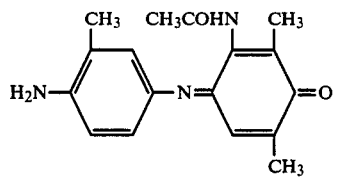

To a solution containing 0.02 mole (3.58 g) of 2,6-dimethyl 3-acetylamino phenol in 48 cc of acetone there is added 0.02 mole (3.90 g) of the dihydrochloride of paratoluene diamine in 35 cc of water to which have been added 13 cc of ammonia (22° Bé). Into this resulting mixture there is added, little by little, with agitation, 0.03 mole (6.84 g) of ammonium persulfate dissolved in 15 cc of water. The resulting reaction mixture is permitted to stand for 15 minutes at ambient temperature. By filtering 2.94 g of the above indoaniline are recovered, which after washing with water and with acetone, followed by recrystallization from a mixture of pyridine and water, exhibited a melting point of 185° C.

| Analysis | Calculated for C₁₇H₁₉N₃O₂ | Found | |
|---|---|---|---|
| C % | 68.68 | 68.42 | 68.44 |
| H % | 6.39 | 6.44 | 6.53 |
| N % | 14.14 | 13.89 | 13.89 |

EXAMPLE 47

Preparation of N-[(4'-amino 2'-methoxy 5'-methyl)-phenyl]3-acetylamino 2,6-dimethyl benzoquinone imine having the formula

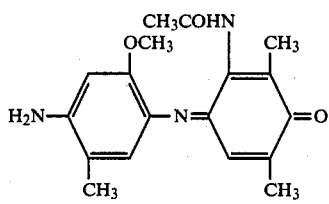

0.03 mole (5.37 g) of 2,6-dimethyl, 3-acetylamino phenol is dissolved in 200 cc of water to which have been added 90 cc of ammonia (22° Bé). To this solution there are simultaneously added through two dropping funnels, a solution of 0.03 mole (6.75 g) of the dihydrochloride of 2-methoxy 5-methyl paraphenylenediamine through one funnel and a solution of 0.06 mole (19.75 g) of potassium ferricyanide in 200 cc of water through the other funnel, the reaction mixture being maintained at a temperature not greater than about 10° C. After the addition of the two above solutions is completed, the reaction mixture is permitted to stand for about 20 minutes at about 10° C. After filtering 4.40 g of the above indoaniline are recovered, which after recrystallization from a mixture of dimethylformamide and water, exhibited a melting point of 236° C.

| Analysis | Calculated for C₁₈H₂₁N₃O₃ | Found | |
|---|---|---|---|
| C % | 66.05 | 65.79 | 65.69 |
| H % | 6.42 | 6.39 | 6.34 |
| N % | 12.84 | 13.08 | 13.00 |

EXAMPLE 48

Preparation of N-[4'-amino 2'-methoxy)phenyl]3-acetylamino benzoquinone imine having the formula

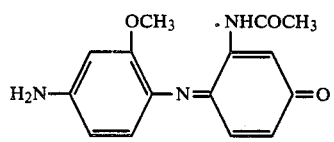

Initially, there is dissolved 0.01 mole (2.11 g) of the dihydrochloride of methoxy paraphenylenediamine in 50 cc of water. Separately, there is dissolved 0.01 mole (1.51 g) of m-acetylaminophenol in 100 cc of water to which have been added 30 cc of ammonia (22° Bé). The above two solutions are then mixed together and to this resulting mixture there is slowly added, with agitation, 0.02 mole (6.58 g) of potassium ferricyanide in 50 cc of water while maintaining the reaction temperature between 5° and 10° C. There are then recovered from the reaction mixture, by filtering, 1.42 g of the above indoaniline. After washing the same with water and after recrystallization in a mixture of pyridine and water, the product was chromatographically pure and exhibited a melting point of 241° C.

| Analysis | Calculated for C₁₅H₁₅N₃O₃ | Found | |
|---|---|---|---|
| C % | 63.15 | 62.86 | 62.96 |
| H % | 5.26 | 5.39 | 5.36 |
| N % | 14.73 | 14.92 | 14.83 |

Molecular weight calculated for $C_{15}H_{15}N_3O_3 = 285$.
Molecular weight found by potentiometric determination effected in acetic acid with perchloric acid $= 289$.

EXAMPLE 49

The following dye solution is prepared:

| Compound of example 42 | 0.2 g |
|---|---|
| Ethyl alcohol (96°) | 50 g |
| Ammonia (22° Be') q.s.p. | pH 10 |
| Water q.s.p. | 100 g |

This solution is applied to bleached hair at ambient temperature. After 20 minutes, the hair is rinsed and shampooed and there is obtained a very clear jade green coloration.

EXAMPLE 50

The following dye solution is prepared:

| The compound of Example 44 | 0.05 g |
|---|---|
| Copolymer of 10% crotonic acid-90% vinyl acetate (M.W. 45,000–50,000) | 2 g |
| Ethyl alcohol (96°) q.s.p. | 50° |
| Triethanolamine q.s.p. | pH 7 |
| Water q.s.p. | 100 g |

This solution is applied as a hair setting lotion on 100% white hair and imparts thereto a pearlescent rose coloration lightly tinted mauve.

EXAMPLE 51

The following solution is prepared:

| The compound of Example 47 | 0.05 g |
|---|---|
| Copolymer of crotonic acid-vinyl acetate (as in Example 50) | 2 g |
| Ethyl alcohol (96°) q.s.p. | 50° |
| Triethanolamine q.s.p. | pH 7 |
| Water q.s.p. | 100 g |

This solution is applied as a hair setting lotion to bleached hair and imparts thereto a silvery pastel blue coloration.

EXAMPLE 52

The following solution is prepared:

| Compound of Example 41 | 0.10 g |
|---|---|
| Copolymer of crotonic acid and vinyl acetate (as in Example 50) | 2 g |

| Ethyl alcohol (96°) q.s.p. | 50° |
|---|---|
| Triethanolamine q.s.p. | pH 7 |
| Water q.s.p. | 100 g |

This solution is applied as a hair setting lotion to bleached hair and imparts thereto a very luminous deep blue coloration.

EXAMPLE 53

The following dye solution is prepared:

| The compound of Example 44 | 0.5 g |
|---|---|
| Ethyl alcohol (96°) | 25 g |
| Water q.s.p. | 100 g |
| Ammonia (22° Be') q.s.p. | pH 10 |

This solution is applied to bleached hair at ambient temperature and after 20 minutes the hair is rinsed and shampooed. A bright crimson rose coloration is obtained.

EXAMPLE 54

The following dye solution is prepared:

| The compound of Example 41 | 0.3 g |
|---|---|
| Ethyl alcohol (96°) | 25 g |
| Water q.s.p. | 100 g |
| Ammonia (22° Be') q.s.p. | pH 10 |

This solution is applied to 95% naturally white hair at ambient temperature and after 20 minutes the hair is rinsed and shampooed. A blue grey coloration is obtained.

EXAMPLE 55

The following dye solution is prepared:

| The compound of Example 42 | 0.1 g |
|---|---|
| Copolymer of crotonic acid-vinyl acetate (as in Example 50) | 2 g |
| Ethyl alcohol (96°) q.s.p. | 50° |
| Water q.s.p. | 100 g |
| Triethanolamine q.s.p. | pH 7 |

This solution is applied as a hair setting lotion to bleached hair and imparts thereto a deep turquoise blue coloration.

EXAMPLE 56

The following hair dye solution is prepared:

| Compound of Example 45 | 0.05 g |
|---|---|
| Copolymer of crotonic acid-vinyl acetate (Example 50) | 2 g |
| Ethyl alcohol (96°) q.s.p. | 50° |
| Water q.s.p. | 100 g |
| Triethanolamine q.s.p. | pH 7 |

This siolution is applied as a hair setting lotion on bleached hair and imparts thereto a clear and pearlescent turqu blue coloration.

EXAMPLE 57

The following dye solution is prepared:

| Compound of Example 43 | 0.05 g |
|---|---|
| Copolymer of crotonic acid and vinyl acetate (as in Example 50) | 2 g |
| Ethyl alcohol (96°) q.s.p. | 50° |
| Water q.s.p. | 100 g |
| Triethanolamine q.s.p. | pH 7 |

This solution is applied as a hair setting lotion on bleached hair and imparts thereto a light pearlescent mauve coloration.

EXAMPLE 58

The following solution is prepared:

| The Compound of Example 44 | 0.4 g |
|---|---|
| Ethyl alcohol (96°) | 25 g |
| Water q.s.p. | 100 g |
| pH | 7 |

This solution is applied at 30° C. to 95% natural white hair. After 20 minutes the hair is rinsed and shampooed and a violet coloration is obtained.

EXAMPLE 59

The following solution is prepared:

| Compound of Example 45 | 0.05 g |
|---|---|
| Copolymer of crotonic acid and vinyl acetate (as in Example 50) | 2 g |
| Ethyl alcohol (96°) q.s.p. | 50° |
| Water q.s.p. | 100 g |
| Triethanolamine q.s.p. | pH 7 |

This solution is applied as a hair setting lotion to bleached hair and imparts thereto a wisteria-like coloration.

EXAMPLE 60

The following solution is prepared:

| Compound of Example 46 | 0.1 g |
|---|---|
| Nitro-orthophenylenediamine | 0.05 g |
| Copolymer of crotonic acid-vinyl acetate (as in Example 50) | 2 g |
| Ethyl alcohol (96°) q.s.p. | 50° |
| Water q.s.p. | 100 g |
| Triethanolamine q.s.p. | pH 7 |

This solution is applied as a hair setting lotion to bleached hair and imparts thereto a verdigris coloration.

EXAMPLE 61

The following solution is prepared:

| Compound of Example 41 | 0.025 g |
|---|---|
| Nitroparaphenylenediamine | 0.05 g |
| Copolymer of crotonic acid-vinyl acetate (As in Example 50) | 2 g |
| Ethyl alcohol (96°) q.s.p. | 50° |
| Water q.s.p. | 100 g |
| Triethanolamine q.s.p. | pH 7 |

This solution is applied as a hair setting lotion on bleached hair imparting thereto an ash gray coloration which is heavily tinted mauve.

EXAMPLE 62

The following solution is prepared:

| | |
|---|---|
| The compound of Example 44 | 0.1 g |
| N—[(4'-amino 3',5'-dimethyl 2'-methoxy) phenyl] 2,6-dimethyl benzoquinone imine | 0.05 g |
| Copolymer of crotonic acid-vinyl acetate (as in Example 50) | 2 g |
| Ethyl alcohol (96°) q.s.p. | 50° |
| Water q.s.p. | 100 g |
| Triethanolamine q.s.p. | pH 7 |

This solution is applied as a hair setting lotion to bleached hair and imparts thereto a deep mauve coloration.

EXAMPLE 63

The following solution is prepared:

| | |
|---|---|
| Compound of Example 48 | 0.1 g |
| Copolymer of crotonic acid and vinyl acetate (as in Example 50) | 2 g |
| Ethyl alcohol (96°) q.s.p. | 50° |
| Water q.s.p. | 100 g |
| Triethanolamine q.s.p. | pH 7 |

This solution is applied as a hair setting lotion to bleached hair and imparts thereto a lavender blue coloration with silvery glints.

EXAMPLE 64

Preparation of N-[(4'-amino)phenyl]-3-ureido benzoquinone imine, having the formula

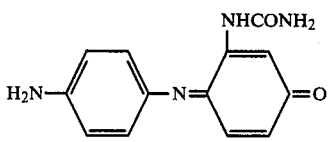

There is dissolved 0.25 mole (38 g) of 3-ureido phenol in 800 cc of isopropyl alcohol, 800 cc of ammonia (22° Bé) and 2500 cc of ice water. To this solution, cooled in a mixture of ice and salt there are added, simultaneously and little by little through two dropping funnels, a solution of 0.25 mole (45.25 g) of paraphenylene diamine dihydrochloride in 400 cc of water through one of the funnels, and a solution of 0.5 mole (114 g) of ammonium persulfate in 400 cc of water through the other funnel, with agitation. At the end of this addition step, agitation is continued for 15 minutes. The reaction mixture is then filtered to recover the above benzoquinone imine which is then washed with water and dried under a vacuum, the resulting chromatographically pure indoaniline exhibiting a melting point of 265° C.

| Analysis | Calculated for $C_{13}H_{12}N_4O_2$ | Found | |
|---|---|---|---|
| C % | 60.93 | 60.64 | 60.69 |
| H % | 4.72 | 4.89 | 4.99 |
| N % | 21.87 | 21.64 | 21.72 |

EXAMPLE 65

Preparation of N-[(4'-amino)phenyl]-2-methyl-5-ureido benzoquinone imine having the formula

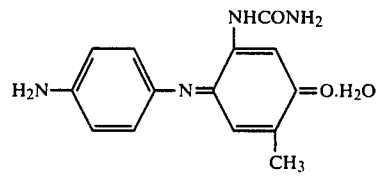

There is dissolved 0.025 mole (4.15 g) of 2-methyl-5-ureido phenol in 100 cc of isopropyl alcohol to which have been added 200 cc of ice water and 100 cc of ammonia (22° Bé). To this solution there is added 0.025 mole (4.52 g) of paraphenylene diamine dihydrochloride and then, little by little, and with agitation, 0.05 mole (114 g) of ammonium persulfate in 40 cc of water. Agitation of the resulting mixture is continued for 15 minutes. The reaction mixture is then filtered to recover the above benzoquinone imine which is then washed with water. After recrystallizing the above indoaniline in a mixture of dimethylformamide and water, and drying under a vacuum at ambient temperature, the product thus obtained melts with decomposition at 255° C.

| Analysis | Calculated for $C_{14}H_{14}N_4O_2H_2O$ | Found | |
|---|---|---|---|
| C % | 58.32 | 58.45 | 58.73 |
| H % | 5.59 | 5.77 | 5.69 |
| N % | 19.44 | 19.57 | 19.67 |

EXAMPLE 66

Preparation of N-[(4'-amino)phenyl]-2,6-dimethyl-5-ureido benzoquinone imine, having the formula

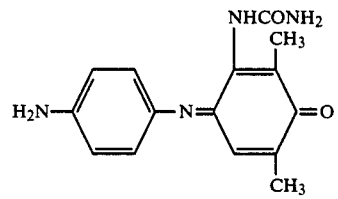

There are dissolved 0.25 mole (45.0 g) of 2,6-dimethyl-5-ureido phenol and 0.25 mole (45.2 g) of paraphenylenediamine dihydrochloride in 1 liter of isopropyl alcohol to which have been added 1250 cc of ice water and 900 cc of ammonia (22° Bé). There is then added to this resulting solution, little by little and with agitation, 0.5 mole (114 g) of ammonium persulfate in 500 cc of water. When this addition step is completed, agitation of the reaction mixture is continued for 15 minutes, at which time the reaction mixture is then filtered to recover the above benzoquinone imine which is washed with water and dried under a vacuum at ambient temperature. The resulting indoaniline is chromatographically pure and melts with decomposition at 253° C.

| Analysis | Calculated For $C_{15}H_{16}N_4O_2$ | Found | |
|---|---|---|---|
| C % | 63.36 | 63.42 | 63.53 |
| H % | 5.67 | 5.79 | 5.68 |
| N % | 19.71 | 19.75 | 19.69 |

EXAMPLE 67

Preparation of N-[(4'-amino-2'-methoxy-5'-methyl)-phenyl]-3-ureido benzoquinone imine, having the formula

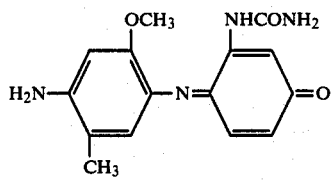

There is dissolved 0.12 mole (18.24 g) of 3-ureido phenol in 400 cc of isopropyl alcohol, 400 cc of ammonia (22° Bé) and 1250 cc of ice water. To this solution, cooled in an ice-salt mixture, there are added, simultaneously and little by little, through two dropping funnels, a solution of 0.12 mol (27 g) of 2-methyl-5-methoxy paraphenylene diamine dihydrochloride in 200 cc of water through one of the funnels, and a solution of 0.24 mole (55 g) of ammonium persulfate in 100 cc of water through the other funnel, with agitation. At the end of this addition step, agitation is continued for 15 minutes. The reaction mixture is then filtered to recover the above benzoquinone imine which is then washed with water and dried under a vacuum, the resulting chromatographically pure indoaniline exhibiting a melting point of 285° C.

| Analysis | Calculated For $C_{15}H_{16}O_3N_4$ | Found | |
|---|---|---|---|
| C % | 60.00 | 60.25 | 60.28 |
| H % | 5.33 | 5.43 | 5.47 |
| N % | 18.66 | 18.50 | 18.46 |

EXAMPLE 68

Preparation of N-[(4'-amino-2'-methoxy-5'-methyl)-phenyl]-2-methyl-5-ureido benzoquinone imine, having the formula

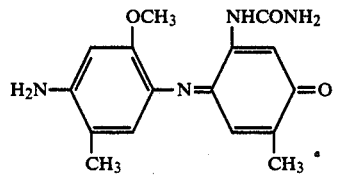

There is dissolved 0.5 mole (83 g) of 2-methyl-5-ureido phenol into two liters of isopropyl alcohol to which have been added six liters of ice water and two liters of ammonia (22° Bé). To this solution there is added 0.5 mole (112.5 g) of 2-methyl-5-methoxy paraphenylene diamine dihydrochloride in 800 cc of water. Then little by little, and with agitation there is added 1 mole (228 g) of ammonium persulfate in 400 cc of water. The reaction mixture is then filtered to recover the above benzoquinone imine which is then washed with water, yielding 120 g of crude indoaniline. After recrystallizing the same in a mixture of dimethylformamide and water and drying the same in a vacuum at ambient temperature, the resulting product melts with decomposition at 248° C.

| Analysis | Calculated For $C_{16}H_{18}N_4O_3$ | Found | |
|---|---|---|---|
| C % | 61.13 | 60.83 | 60.78 |
| H % | 5.77 | 5.83 | 5.68 |
| N % | 17.83 | 18.00 | 18.03 |

EXAMPLE 69

Preparation of N-[(4'-amino-2',5'-dimethyl)phenyl]-2-ureido benzoquinone imine, having the formula

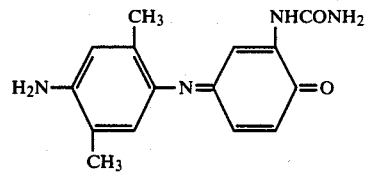

There are dissolved 0.01 mole (1.36 g) of 2,5-dimethyl paraphenylene diamine and 0.01 mole (1.52 g) 2-ureido phenol in 15 cc of ice water. To the resulting solution, cooled in an ice-salt mixture, there is added, little by little, with agitation, 0.02 mole (4.56 g) of ammonium persulfate in 15 cc of water. At the termination of this addition step, the reaction mixture is filtered to recover the above benzoquinone imine which is then washed with water and dried under a vacuum. The resulting indoaniline, which is chromatographically pure, melts with decomposition at 195° C.

| Molecular weight calculated for $C_{15}H_{16}N_4O_2$ | 284 | | |
|---|---|---|---|
| Molecular weight found by potentiometric determination effected in acetic acid with perchloric acid | 283 | | |

| Analysis | Calculated for $C_{15}H_{16}N_4O_2$ | Found | |
|---|---|---|---|
| C % | 63.36 | 69.98 | 62.87 |
| H % | 5.67 | 5.82 | 5.75 |
| N % | 19.71 | 19.90 | 19.91 |

EXAMPLE 70

The following dye solution is prepared:

| Compound of Example 64 | 0.2 g |
|---|---|
| Copolymer of 10% crotonic acid-90% vinyl acetate (M.W. 45,000–50,000) | 2 g |
| Ethyl alcohol (96°) | 50 g |
| Triethanolamine q.s.p. | pH 7 |
| Water, q.s.p. | 100 g |

This solution is applied as a hair setting lotion on bleached hair and after drying with warm air, imparts thereto a luminous violet coloration.

EXAMPLE 71

The following dye solution is prepared:

| Compound of Example 65 | 0.1 g |
|---|---|
| Copolymer of 10% crotonic acid-90% vinyl acetate (M.W. 45,000–50,000) | 1.61 g |
| Ethyl alcohol (96°) | 40.3 g |
| Triethanolamine, q.s.p. | pH 8.5 |

-continued

| | |
|---|---|
| Water, q.s.p. | 100 g |

This solution is applied as a hair setting lotion on bleached hair. After drying the same with warm air, there is imparted to the hair a light mauve coloration.

EXAMPLE 72

The following dye solution is prepared:

| | |
|---|---|
| Compound of Example 66 | 0.05 g |
| Copolymer of 10% crotonic acid-90% vinyl acetate (M.W. 45,000–50,000) | 1.35 g |
| Ethyl alcohol (96°) | 33.8 g |
| Triethanolamine, q.s.p. | pH 9 |
| Water, q.s.p. | 100 g |

This solution is applied as a hair setting lotion to bleached hair which after drying with warm air, imparts thereto a mauve coloration.

EXAMPLE 73

The following dye solution is prepared:

| | |
|---|---|
| Compound of Example 67 | 0.05 g |
| Copolymer of 10% crotonic acid-90% vinyl acetate (M.W. 45,000–50,000) | 1.35 g |
| Ethyl alcohol (96°) | 33.8 g |
| Triethanolamine, q.s.p. | pH 7 |
| Water, q.s.p. | 100 g |

This solution is applied as a hair setting lotion on bleached hair. After drying with warm air, there is imparted thereto a forget-me-not blue coloration.

EXAMPLE 74

The following dye solution is prepared:

| | |
|---|---|
| Compound of Example 68 | 0.1 g |
| Copolymer of 10% crotonic acid-90% vinyl acetate (M.W. 45,000–50,000) | 1.78 g |
| Ethyl alcohol (96°) | 44.6 g |
| Triethanolamine, q.s.p. | pH 5.5 |
| Water, q.s.p. | 100 g |

This solution is applied as a hair setting lotion on bleached hair. After drying with warm air, there is imparted thereto a steel gray blue coloration.

EXAMPLE 75

The following dye solution is prepared:

| | |
|---|---|
| Compound of Example 64 | 0.2 g |
| Polyvinylpyrrolidone (M.W. 40,000) | 1 g |
| Ethyl alcohol (96°) | 20 g |
| Triethanolamine, q.s.p. | pH 6 |
| Water, q.s.p. | 100 g |

This solution is applied as a hair setting lotion on white hair. After drying it imparts thereto a violet gray coloration.

EXAMPLE 76

The following dye solution is prepared:

| | |
|---|---|
| Compound of Example 64 | 0.2 g |

-continued

| | |
|---|---|
| Polyvinylpyrrolidone (M.W. 40,000) | 3 g |
| Ethyl alcohol (96°) | 20 g |
| Triethanolamine, q.s.p. | pH 10 |
| Water, q.s.p. | 100 g |

This solution is applied as a hair setting lotion on white hair and imparts thereto a violet coloration.

EXAMPLE 77

The following dye solution is prepared:

| | |
|---|---|
| Compound of Example 64 | 0.2 g |
| Copolymer of 40% polyvinylpyrrolidone-60% vinyl acetate (M.W. 40,000) | 1 g |
| Ethyl alcohol (96°) | 50 g |
| Triethanolamine, q.s.p. | pH 6 |
| Water, q.s.p. | 100 g |

This solution is applied as a hair setting lotion on white hair and imparts thereto a wisteria-like coloration.

EXAMPLE 78

The following dye isolation is prepared:

| | |
|---|---|
| Compound of Example 64 | 0.2 g |
| Copolymer of 70% polyvinylpyrrolidone 30% vinyl acetate (M.W. 40,000) | 3 g |
| Ethyl alcohol (96°) | 50 g |
| Triethanolamine, q.s.p. | pH 10 |
| Water, q.s.p. | 100 g |

This solution is applied as a hair setting lotion on white hair and imparts thereto a purplish violet coloration.

EXAMPLE 79

The following dye solution is prepared:

| | |
|---|---|
| Compound of Example 67 | 0.05 g |
| Copolymer of 70% polyvinylpyrrolidone-30% vinyl acetate (M.W. 40,000) | 3 g |
| Ethyl alcohol (96°) | 20 g |
| Triethanolamine, q.s.p. | pH 7 |
| Water, q.s.p. | 100 g |

This solution is applied as a hair setting lotion on white hair and imparts thereto a pearlescent gray blue coloration.

EXAMPLE 80

The following dye solution is prepared:

| | |
|---|---|
| Compound of Example 68 | 0.1 g |
| Copolymer of 70% polyvinylpyrrolidone-30% vinyl acetate (M.W.160,000) | 2 g |
| Ethyl alcohol (96°) | 40 g |
| Triethanolamine, q.s.p. | pH 5 |
| Water, q.s.p. | 100 g |

This solution is applied as a hair setting lotion on white hair and imparts thereto a steel gray blue coloration.

EXAMPLE 81

The following dye solution is prepared:

| | |
|---|---|
| Compound of Example 65 | 0.1 g |
| Terpolymer of 80% vinyl acetate-15% allyl stearate-5% allyloxy acetic acid (made in accordance with SN 747,460, filed 25-7-68 now U.S. Pat. No. 3,613,550) | 1 g |
| Ethyl alcohol (96°) | 50 g |
| Triethanolamine, q.s.p. | pH 8.5 |
| Water, q.s.p | 100 g |

This solution is applied as a hair setting lotion on white hair and imparts thereto a pearlescent mauve coloration.

EXAMPLE 82

The following dye solution is prepared:

| | |
|---|---|
| Compound of Example 66 | 0.05 g |
| Terpolymer of 20% methyl methacrylate-23% stearyl methacrylate-57% dimethyl methacrylate (made in accordance with SN 287,845 filed 11-9-72 now U.S. Pat. No. 3,934,595) | 1 g |
| Ethyl alcohol (96°) | 50 g |
| Triethanolamine, q.s.p. | pH 9 |
| Water, q.s.p. | 100 g |

This solution is applied as a hair setting lotion on white hair and imparts thereto a silvery mauve coloration.

EXAMPLE 83

The following dye solution is prepared:

| | |
|---|---|
| Compound of Example 69 | 0.005 g |
| Polyvinylpyrrolidone (M.W. 40,000) | 2 g |
| Ethyl alcohol (96°) | 25 g |
| Triethanolamine, q.s.p. | pH 7.5 |
| Water, q.s.p. | 100 g |

This solution is applied as a hair setting lotion on white hair and imparts thereto a turquoise coloration with ash glints.

What is claimed is:

1. An indoaniline having the formula

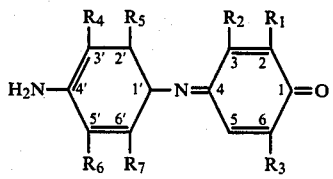

wherein $R_1$ and $R_3$ each independently represent a member selected from the group consisting of hydrogen, lower alkyl, lower alkoxy, a ureido radical and —NHCOR wherein R is lower alkyl;

$R_2$ is selected from the group consisting of hydrogen, lower alkyl, lower alkoxy, a ureido radical, —NHCOR wherein R is lower alkyl, and —NHR$_8$ wherein R$_8$ is selected from the group consisting of hydrogen, lower alkyl, hydroxy lower alkyl and carbamylmethyl, with the proviso that when $R_2$ is —NHR$_8$, $R_3$ is not hydrogen;

$R_4$, $R_5$, $R_6$ and $R_7$ each independently represent a member selected from the group consisting of hydrogen, halogen, lower alkyl and lower alkoxy, with the further proviso that at least two of $R_1$ to $R_7$ are other than hydrogen and that $R_5$ and $R_7$ are not simultaneously chlorine.

2. An indoaniline having the formula

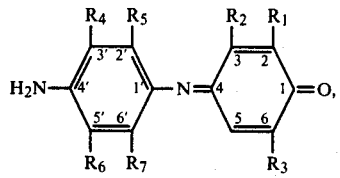

wherein $R_1$ and $R_3$ each independently represent a member selected from the group consisting of hydrogen, lower alkyl, a ureido radical and —NHCOR wherein R is lower alkyl;

$R_2$ is selected from the group consisting of hydrogen, lower alkyl, a ureido radical and —NHCOR wherein R is lower alkyl, and —NHR$_8$ wherein R$_8$ is selected from the group consisting of hydrogen, lower alkyl and carbamylmethyl, with the proviso that when $R_2$ is —NHR$_8$, $R_3$ is not hydrogen; and $R_4$, $R_5$, $R_6$ and $R_7$ each independently represent a member selected from the group consisting of hydrogen, halogen, lower alkyl and lower alkoxy, with the further proviso that at least two of $R_1$ to $R_7$ are other than hydrogen and that $R_5$ and $R_7$ are not simultaneously chlorine.

3. An indoaniline selected from the group consisting of:

N-[(4'-amino-3',5'-dimethyl-2'-methoxy)phenyl]benzoquinoneimine,

N-[(4'-amino-3',5'-dimethyl-2'-methoxy)phenyl]2,6-dimethyl benzoquinoneimine,

N-[(4'-amino-3',5'-dimethyl-2'-methoxy)phenyl]2,5-dimethyl benzoquinoneimine,

N-[(4'-amino)phenyl]-5-amino-2-methyl benzoquinoneimine,

N-[(4'-amino-3'-methyl)phenyl]-3-amino-6-methyl benzoquinoneimine,

N-[(4'-amino-2'-methoxy)phenyl]-3-amino-6-methyl benzoquinoneimine,

N-[(4'-amino-3'-chloro)phenyl]-3-amino-6-methyl benzoquinoneimine,

N-[(4'-amino-3',5'-dimethyl-2'-methoxy)phenyl]-3-amino-6-methyl benzoquinoneimine, N-[(4'-amino tetramethyl)phenyl]-5-amino-2-methyl benzoquinoneimine, N-[(4'-amino-2'-methoxy)phenyl]-6-methyl-3-methylamino benzoquinoneimine, N-[(4'-amino-3'-methyl)phenyl]-3-carbamylmethylamino-6-methyl benzoquinoneimine, N-[(4'-amino-3'-methyl)phenyl]-3-amino-2,6-dimethyl benzoquinoneimine, N-[(4'-amino-2'-methoxy)phenyl]-3-amino-2,6-dimethyl benzoquinoneimine, N-[(4'-amino-3'-chloro)phenyl]-3-amino-2,6-dimethyl benzoquinoneimine, N-[(4'-amino-2'-methoxy-5'-methyl)phenyl]-3-amino-2,6-dimethyl benzoquinoneimine, N-[(4'-amino tetramethyl)phenyl]-3-amino-2,6-dimethyl benzoquinoneimine, N-[(4'-amino-3'-methyl)phenyl]-3-acetylamino benzoquinoneimine, N-[(4'-amino-2'-methoxy-5'-methyl)phenyl]-3-acetylamino benzoquinoneimine, N-[(4'-amino)phenyl]-5-acetylamino-2-methyl benzoquinoneimine,
N-[(4'-amino-3'-methyl)phenyl]-3-acetylamino-6-methyl benzoquinoneimine,
N-[(4'-amino-2'-methoxy)phenyl]-3-acetylamino-6-methyl benzoquinoneimine,
N-[(4'-amino-3'-chloro)phenyl]-3-acetylamino-6-methyl benzoquinoneimine,
N-[(4'-amino-2'-methoxy-5'-methyl)phenyl]-3-acetylamino-6-methyl benzoquinoneimine,
N-[(4'-aminotetramethyl)phenyl]-3-acetylamino-6-methyl benzoquinoneimine,
N-[(4'-amino-3'-methyl)phenyl]-2-acetylamino benzoquinoneimine,
N-[(4'-amino)phenyl]-3-acetylamino-2,6-dimethyl benzoquinoneimine,
N-[(4'-amino-2',5'-dimethoxy)phenyl]-3-amino-6-methyl benzoquinoneimine,
N-[(4'-amino-2'-methoxy)phenyl]-2,6-dimethyl benzoquinoneimine,
N-[(4'-amino-2',5'-dimethoxy)phenyl]-2,6-dimethyl benzoquinoneimine,
N-[(4'-amino-2'-methoxy-5'-methyl)phenyl]-2-methyl-5-amino benzoquinoneimine,
N-[(4'-amino)phenyl]-3-amino-2,6-dimethyl benzoquinoneimine,
N-[(4'-amino-2',5'-dimethoxy)phenyl]-2-methyl-5-acetylamino benzoquinoneimine,
N-[(4'-amino-3'-methyl)phenyl]-3-acetylamino-2,6-dimethyl benzoquinoneimine,
N-[(4'-amino-2'-methoxy-5'-methyl)phenyl]-3-acetylamino-2,6-dimethyl benzoquinoneimine,
N-[(4'-amino-2'-methoxy)phenyl]-3-acetylamino benzoquinoneimine,
N-[(4'-amino)phenyl]-3-ureido benzoquinoneimine,
N-[(4'-amino)phenyl]-2-methyl-5-ureido benzoquinoneimine,
N-[(4'-amino)phenyl]-2,6-dimethyl-5-ureido benzoquinoneimine,
N-[(4'-amino-2'-methoxy-5'-methyl)phenyl]-3-ureido benzoquinoneimine,
N-[(4'-amino-2'-methoxy-5'-methyl)phenyl]-2-methyl-5-ureido benzoquinoneimine and
N-[(4'-amino-2',5'-dimethyl)phenyl]-2-ureido benzoquinoneimine.

* * * * *